United States Patent
Aigner et al.

(10) Patent No.: US 9,242,217 B2
(45) Date of Patent: Jan. 26, 2016

(54) PROCESS AND APPARATUS FOR CONTINUOUS HIGH TEMPERATURE SHORT-TIME ALKOXYLATION (ETHOXYLATION, PROPOXYLATION) OF CHEMICAL SUBSTANCES WITH ACTIVE HYDROGEN ATOMS

(75) Inventors: Rudolf Aigner, Kastl (DE); David Hirsch, Fullinsdorf (CH); Alfred Lagnaz, Liestal (CH)

(73) Assignee: Buss ChemTech AG, Pratteln (CH)

( * ) Notice: Subject to any disclaimer, the term of this patent is extended or adjusted under 35 U.S.C. 154(b) by 318 days.

(21) Appl. No.: 13/879,224

(22) PCT Filed: Oct. 12, 2011

(86) PCT No.: PCT/EP2011/067808
§ 371 (c)(1),
(2), (4) Date: Jul. 5, 2013

(87) PCT Pub. No.: WO2012/049210
PCT Pub. Date: Apr. 19, 2012

(65) Prior Publication Data
US 2013/0289315 A1    Oct. 31, 2013

(30) Foreign Application Priority Data
Oct. 13, 2010  (EP) .................................... 10187427

(51) Int. Cl.
*B01J 8/06*    (2006.01)
*C07C 41/03*   (2006.01)
*B01J 4/00*    (2006.01)
*B01J 14/00*   (2006.01)
*B01J 19/00*   (2006.01)
*B01J 19/24*   (2006.01)
*C08G 65/26*   (2006.01)

(52) U.S. Cl.
CPC  *B01J 8/067* (2013.01); *B01J 4/002* (2013.01); *B01J 4/005* (2013.01); *B01J 14/00* (2013.01); *B01J 19/002* (2013.01); *B01J 19/006* (2013.01); *B01J 19/247* (2013.01); *B01J 19/2425* (2013.01); *C07C 41/03* (2013.01); *C08G 65/2696* (2013.01)

(58) Field of Classification Search
None
See application file for complete search history.

(56) References Cited

U.S. PATENT DOCUMENTS

| 3,577,224 A * | 5/1971 | Hess et al. ................. 422/132 |
| 4,183,897 A | 1/1980 | Lanteri |
| 5,510,542 A | 4/1996 | Jakobson et al. |
| 5,911,958 A | 6/1999 | Dahl |
| 6,977,064 B1 | 12/2005 | Adris et al. |
| 2002/0147370 A1 | 10/2002 | Hinz et al. |
| 2008/0306295 A1 | 12/2008 | Aigner et al. |

FOREIGN PATENT DOCUMENTS

| DE | 735418 | 5/1943 |
| DE | 4128827 A1 | 3/1993 |
| DE | 4228147 A1 | 3/1994 |
| DE | 10054462 A1 | 6/2002 |
| DE | 102005060816 B3 | 3/2007 |

* cited by examiner

*Primary Examiner* — Rosalynd Keys
(74) *Attorney, Agent, or Firm* — The Webb Law Firm

(57) ABSTRACT

Disclosed is a process for continuously reacting liquid alkylene oxide with a liquid substance including an organic compound with active hydrogen atoms and a catalyst in a reactor.

22 Claims, 7 Drawing Sheets

Top view

Top view

PROCESS AND APPARATUS FOR CONTINUOUS HIGH TEMPERATURE SHORT-TIME ALKOXYLATION (ETHOXYLATION, PROPOXYLATION) OF CHEMICAL SUBSTANCES WITH ACTIVE HYDROGEN ATOMS

BACKGROUND OF THE INVENTION

1. Field of the Invention

The present invention relates to a process and an apparatus for continuously reacting liquid alkylene oxide with a liquid substance comprising an organic compound with one or more active hydrogen atoms and a catalyst selected from alkali metal hydroxides and alkali metal alcoholates, hereinafter also referred to as the "liquid catalyzed raw material", in a reactor selected from (a) a tubular reactor comprising at least one reaction tube providing a reaction space inside of said tube, and
(b) an annular-gap reactor comprising an outer tube and an inner tube, longitudinally inserted into said outer tube, which form an annular reaction gap extending between the inner of the outer tube, which forms the outer boundary of the reaction gap, and the outer surface of the inner tube, which forms the inner boundary of the reaction gap.

2. Description of Related Art

DE 735 418 discloses a process, wherein a tube reactor comprising one reaction tube is used for a continuous alkoxylation of organic hydroxyl compounds, in particular alkyl phenols, and to a mixture of sodium hydroxide and said organic hydroxyl compound in parts at more than one location along the reaction tube. The distance of the locations for adding the liquid alkylene oxide from one another and the quantity of alkylene oxide supplied at the single locations is chosen such that the reaction temperature can be kept low enough, so that the reaction temperature in the tube does not significantly rise above 200° C. and undesired side reactions can be avoided. In case of working the process e.g. with two feeding locations for alkylene oxide, the organic hydroxyl compound is mixed with about one half of the total required amount of liquid alkylene oxide and the mixture is supplied with a high-pressure pump into a first section of the tube for reaction. After passing said first section, the reaction product is removed from the streaming tube and, after intermediate cooling, mixed with the remaining quantity of the required liquid alkylene oxide and this mixture is supplied with a further high-pressure pump to a second section of the streaming tube and is further reacted to the final product in said section which is then removed. The disclosed process however has many disadvantages including, in particular, that a reactor tube of 200 meter length is required, high pressures over 100 bar have to be maintained in the reaction tube in order to avoid an immediate vaporization of the supplied alkylene oxide and the quantity of alkylene oxide supplied at each feeding location has to be controlled by separate mass flow controllers. Furthermore, this reactor can only be used on a pilot plant scale where the use of a single reaction tube is sufficient, whereas the use of a bundle of reaction tubes, as required for production purposes, would require a multitude of alkylene oxide inlets in each reaction tube of the bundle, each with a mass flow controller. These technical efforts for controlling the alkoxylation are so expensive, that this process has never achieved acceptance in industrial practice.

DE 10054462 describes a similar continuous alkoxylation method, wherein relatively small quantities of liquid ethylene oxide are fed into a tubular reactor or in a tube bundle reactor at a large number of different locations along of the reaction tube (in the Example of this document e.g. at 15 locations). Feeding many small quantities of alkylene oxide is required in order to avoid a runaway of the reactor caused by uncontrolled reaction of the ethylene oxide at the feeding points because of the slow mixing speed of the reactants and the common cooling of all sections along the reaction tube which does not allow a specific control of the temperature in each section. In addition, this process design has again the disadvantage that the alkylene oxide flow is to be measured separately for each feeding location.

US 2008/0306295 claiming the priority of DE102005060816 describes a continuous multi-step process which is specifically designed for carrying out rapid, highly exothermic reactions between a gaseous and a liquid reactant, in particular for reacting a $SO_3$/air mixture with liquid organic compounds including, among several other compounds, alkyl phenols and their alkylene oxide derivatives. The reaction is performed in a reactor selected from (a) a tubular reactor comprising at least one reaction tube providing a reaction space inside of said tube, and
(b) an annular-gap reactor comprising an outer tube and an inner tube, longitudinally inserted into said outer tube, which form an annular reaction gap extending between the inner surface of the outer tube, which forms the outer boundary of the reaction gap, and the outer surface of the inner tube, which forms the inner boundary of the reaction gap, which reactor (a) or (b) is a thin layer falling-film reactor and is connected with a source of a gaseous $SO_3$/air mixture, wherein (1) the gaseous $SO_3$/air mixture is supplied to said reactor via a single inlet socket and the $SO_3$/air mixture is split before entering the reaction space or gap into a first and second part
(2) said first part of the $SO_3$/air mixture enters the reaction space or gap of said reactor (a) or (b) at a first location,
(3) the liquid organic compound is supplied as a film onto the inner surfaces of the at least one reaction tube of the tubular reactor (a) or onto the inner surface of the outer tube and/or onto the outer surface of the inner tube of the annular gap reactor (b) at a second location of the reactor, located downstream of said first location, and is brought into contact with the gaseous $SO_3$/air mixture to form a liquid film of the reaction mixture of said reactants moving downstream on said surfaces towards the end of the reactor, and
(4) the $SO_3$/air mixture enters the reactor at said first location over the entire-cross sectional area of the reaction space or gap at said location, and
(5) said second part of the $SO_3$/air mixture is split off at said first location and is channeled from said first location to a third location in the reaction space or gap through a tube in case of a tube reactor (a) or through a double tube, respectively, in case of an annular gap reactor (b), which tube or double tube is inserted into the reaction space or gap, extends from said first location to said third location of the reactor space or gap, respectively, and has a diameter being smaller than the inner diameter of said reaction tube or outer boundary of said reaction gap, thus leaving a reaction space between the outer surface of said tube or double tube, respectively, on one side, and the inner surface of the reaction tube or the outer boundary of the reaction gap, respectively, on the other side,
(6) said third location is located downstream of said second location,
(7) said second part of the $SO_3$/air mixture enters the reaction space or gap of the reactor at said third location and is brought into contact at said third location with the liquid film of the reaction mixture moving downstream on said surfaces towards the end of the reactor and reacts with it on its way to the outlet of the reactor to form the final reaction product.

The disclosed tube reactors have a length of about 10 m (tube diameter 1 inch) and the disclosed ring gap reactors have a length of about 2 m (6.5 mm annular gap width). Whereas reactors of such a length are useful for reacting organic hydroxyl compounds with the very reactive $SO_3$ gas, they have generally been considered to be much too short for reaction of such compounds with liquid alkylene oxides which are much less reactive than $SO_3$ gas.

SUMMARY OF THE INVENTION

It has now been surprisingly found, however, that reactors of the aforementioned design and length can also be used for alkoxylations of liquid organic materials with reactive hydrogen atoms, when some modifications are applied, and that a use of these modified reactors avoids the described disadvantages of the prior art alkoxylation processes, such as high temperature peaks, the danger of a formation of undesired by-products such as dioxane, dark colored end products, the requirement of working at pressures over 100 bar in the reactor, the limitation of many processes to alkoxylation grades of only 4-6 mole alkylene oxide per mole of the liquid organic raw compounds. These modifications include in particular the supply of the liquid organic material with reactive hydrogen atoms into the reactor in a way which almost immediately provides a very intensive mixing of the organic compounds with the liquid alkylkene oxide entered into the reactor, e.g. by use of ring slit nozzles for the supply of the liquid organic material with reactive hydrogen atoms. Further modifications include one or more of the use of static mixer elements at the locations where the reactants are fed into the reactor and downstream thereof which additionally improve the efficacy of the mixing process, the use of two or more separate tempering jackets which allow an efficient control of the reaction temperature in the reactor with a liquid cooling or heating medium and the use of a post reaction zone of a preferably increased inside width as compared to the reaction space. The shorter length of the reactor as compared to the reactors of the prior art with a length of about 200 m results in a very short residence time of the reaction mixture in the reactor (a few minutes as compared to up to 1 hour in the prior art reactor) which in turn results in a significantly reduced production of unwanted side products and accordingly in a significantly improved quality of the end product.

In a first aspect, the invention accordingly relates to a process for continuously reacting liquid alkylene oxide with a liquid substance comprising an organic compound with one or more active hydrogen atoms and a catalyst selected from alkali metal hydroxides and alkali metal alcoholates according to the present invention, wherein the process is performed in a reactor selected from (a) a tubular reactor comprising at least one reaction tube providing a reaction space inside of said tube, and
(b) an annular-gap reactor comprising an outer tube and an inner tube, longitudinally inserted into said outer tube, which form an annular reaction gap extending between the inner surface of the outer tube, which forms the outer boundary of the reaction gap, and the outer surface of the inner tube, which forms the inner boundary of the reaction gap, and wherein (1) the supply of liquid alkylene oxide to the reactor is controlled by a single mass flow controller, the liquid alkylene oxide is fed to said reactor (a) or (b) via a single inlet socket which is connected with a source of liquid alkylene oxide via said mass flow controller and the alkylene oxide is split before entering the reaction space or gap into a first and a second part and, optionally, further parts,
(2) said first part of alkylene oxide enters the reaction space or gap of said reactor (a) or (b) at a first location,
(3) the liquid organic substance is supplied to the interior of the reaction space of said tubular reactor (a) or to the interior of the reaction gap of said annular gap reactor (b) at a second location of the reactor, located at or downstream of said first location, and is intermingled with the liquid alkylene oxide to form a liquid reaction mixture, which moves downstream towards the end of the reactor,
(4) the liquid alkylene oxide enters the reactor at said first location over the entire-cross sectional area of the reaction space or gap at said location,
(5) said second and, optionally, further parts of alkylene oxide are split off at said first location or upstream thereof and are channeled from said first location to a third location and, when further parts of alkylene oxide are split off, to further locations in the reaction space or gap, through a separate tube for each part of alkylene oxide in case of a tube reactor (a), or through a separate double tube, respectively, in case of an annular gap reactor (b), which tube or double tube is inserted into the reaction space or gap, extends from said first location to said third or said further location of the reactor space or gap, respectively, and has a diameter being smaller than the inner diameter of said reaction tube or outer boundary of said reaction gap, thus leaving a reaction space between the outer surface of said tube or double tube, respectively, on one side, and the inner surface of the reaction tube or the outer boundary of the reaction gap, respectively, on the other side,
(6) said third location and optional further locations are located downstream of said second location and have a distance from said second location and from each other in flow direction of the reactor charge,
(7) said second and optional further parts of liquid alkylene oxide enter the reaction space or gap of the reactor at said third location and said optional further locations and are intermingled with said liquid reaction mixture and react with it on its way downstream towards the end of the reactor and
(8) the inner pressure of the reactor is kept at a pressure level where alkylene oxide entering the reactor does not vaporize.

Furthermore, the present invention relates to an apparatus for continuously reacting liquid alkylene oxide with a liquid substance comprising an organic compound with one or more active hydrogen atoms and a catalyst selected from alkali metal hydroxides and alkali metal alcoholates, comprising a reactor selected from
(a) a tubular reactor comprising at least one reaction tube providing a reaction space inside of said tube, and
(b) an annular-gap reactor comprising an outer tube and an inner tube, longitudinally inserted into said outer tube, which form an annular reaction gap extending between the inner surface of the outer tube, which forms the outer boundary of the reaction gap, and the outer surface of the inner tube, which forms the inner boundary of the reaction gap,
and a source of liquid alkylene oxide which is connected via a single mass flow controller to a single inlet socket of said tubular reactor (a) or said annular gap reactor (b) for the alkylene oxide using a line for said alkylene oxide, wherein said reactor comprises
(1) at the reactor head an inlet for the alkylene oxide to the reaction space of the at least one reaction tube or the reaction gap of the annular gap reactor which extends over the entire cross-sectional area of the said reaction space or gap at a first location of said reaction space or gap, (2) a ring slit nozzle for feeding said liquid substance to the interior of the at least one reaction tube of the tubular reactor (a) and mixing it with alkylene oxide, which is located in said reaction tube at a second location at or downstream of said first location of the reaction space, or two ring slit nozzles for feeding said liquid substance to the interior of the reaction gap of said annular gap reactor (b) and mixing it with alkylene oxide, one ring slit nozzle being located in said outer tube and the other in said inner tube, which form the boundaries of the reaction gap, at a second location at or downstream of said first location of the reaction gap, (3) a first tube inserted into each of the at least one reaction tubes in case of a tubular reactor (a), or a double tube inserted into the reaction gap in case of an annular gap reactor (b), which extends from said first location or from a location upstream of said first location in direction of the outlet of said reactor for the reaction product to a third location in the reaction space or gap having a distance from said first and second location and, optional, further tubes inserted into each of the at least one reaction tubes in case of a tubular reactor (a), or further double tubes inserted into the reaction gap in case of an annular gap reactor (b), which further tubes or double tubes extend from said first location or from a location upstream of said first location in direction of the outlet of said reactor for the reaction product to other locations in the reaction space or gap having a distance from said third location and from one another in flow direction of the reactor charge, which first and optional further tubes channel liquid alkylene oxide from said first location to said third and other locations to dispense it at said location to the reaction space or gap, wherein said first and optional further tube(s) or double tube(s) have a diameter being smaller than the inner diameter of said reaction tube or outer boundary of said reaction gap, thus leaving reaction space between the outer surface of each tube or double tube, respectively, on one side, and the inner surface of the reaction tube or the outer boundary of the reaction gap, respectively, on the other side, (4) preferably, one or more static mixing element(s) located at said second location and, optionally, one or more further static mixing element(s) located between said second location and said third location in the reaction space or reaction gap for supporting the intermixture of the liquid alkylene oxide with said liquid substance and/or one or more static mixing element(s) located at said third and/or downstream of said third location in the reaction space or reaction gap for supporting the intermixture of the liquid alkylene oxide with said the liquid reaction mixture formed between said second and third location in the reactor, (5) preferably, two or more, more preferably three, separate tempering, i.e. cooling or heating jackets, which are consecutively in longitudinal direction of the reactor fitted to the reaction tube(s) of said tubular reactor (a) or to the outer and inner tube of the annular-gap reactor (b), the first one of said tempering jackets preferably being partially or completely located at a position between said second and third location, the second one preferably being located directly after said first tempering jacket and partially or completely after said third location and the optional third and further tempering jackets following consecutively after said second tempering jacket, and (6) an outlet for the reaction product at a location in the reaction space or gap which is downstream from all said other locations.

Although it is generally possible to divide the entire quantity of the alkylene oxide reactant into a multitude of parts which are fed at different locations to the reactor, a division into more than two parts is normally not necessary, because up to about 95 percent of the total required alkylene oxide can normally be supplied to the reactor space or gap at one location and the remainder can then easily be supplied at a second location. For example, it is possible to split the total quantity of liquid alkylene oxide reacted with the liquid substance so, that e.g. 10-90% of the alkylene oxide enter the reaction space or gap at the first location and the balance to 100% at said third location. In fact, it is just a particular advantage of the process according to the present invention that it is sufficient to split the total required amount of alkylene oxide into only two parts because, due to one or more measures which can be taken and which are described below, it is possible to control the reaction in a way that high temperature peaks, the danger of a formation of undesired by-products such as dioxane, dark colored end products, the requirement of using pressures of over 100 bar in the reactor and/or the limitation to alkoxylation grades of only 4-6 mole alkylene-oxide per mole of the liquid organic raw compounds can be avoided, although the entire required alkylene oxide is supplied at only two different locations of the reactor space or gap. Limitation to two locations for alkylene oxide and thus only one insert tube or double tube also simplifies the reactor design and is therefore also preferred in view of the reactor design and construction. The use of more than one insert tube or double tube, on the other hand, can additionally reduce the length of the reactors.

With respect to the mentioned preference for a two stage addition of the alkylene oxide to the reactor, many features of the process and apparatus according to the present invention are described in the following using the example of such a two stage process and a two stage reactor. It should be noted however that the described preferred measures can in most cases also be easily applied to a process or apparatus using three or even more different locations for supplying the alkylene oxide to the reactor space or gap and thus requiring two or more insert tubes or double tubes.

DETAILED DESCRIPTION OF THE INVENTION

Figure 1A:
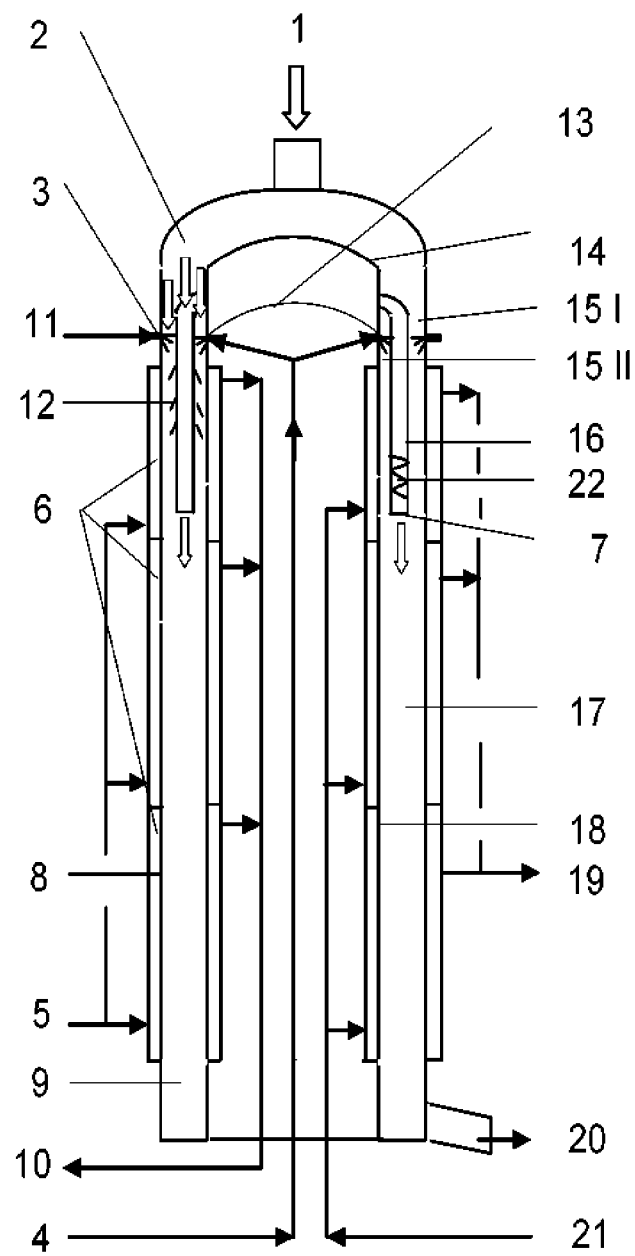
FIG. 1A is a representation of the principle of the invention for a two stage annular-gap reactor with mixing elements.

In its most general form, the apparatus according to the present invention comprises a source of liquid alkylene oxide which is connected with a line for said alkylene oxide and via a single mass flow controller to a single inlet socket for the alkylene oxide to the reactor located near to the reactor head.

The inlet for the liquid alkylene oxide to the reactor space or gap (the main inlet for alkylene oxide) which is connected to said inlet socket and extends over the entire cross-sectional area of the reaction space or gap is located at or upstream of the inlet of the reactor space or gap for the liquid catalyzed raw material to be reacted with the alkylene oxide. The distance between said main inlet for the alkylene oxide and the inlet for the liquid compounds is not critical, but it is preferably rather small or even zero, so that the zone for reaction of the alkylene oxide with said raw material extends over as much of the length of the reactor as possible. The supply of further alkylene oxide to the reactor is effected over one or, optionally, more tubes which are inserted in the reaction tube or tubes of a tubular reactor and are smaller in diameter than the reaction tube(s) or, in case of an annular gap reactor, over one or, optionally, more double tubes inserted in the annular gap. If more than one insert tube or double tube is used, these tubes or double tubes are preferably concentric and the outer diameter of the different tubes or double tubes decreases with increasing length of the respective tubes. These inserted tube(s) or double tube(s) are placed such, that the entrance for liquid alkylene oxide into these tubes or double tubes is also located at or, preferably, upstream of the inlet for the liquid catalyzed raw material to the reaction space or gap of the reactor and preferably coincides with the main inlet for the alkylene oxide, whereas their outlets are located downstream of the inlet for the catalyzed raw material, so that fresh alkylene oxide is provided at the outlet of said tubes to the at least partially reacted mixture of the catalyzed raw materials and the alkylene oxide already supplied to the reaction space or gap upstream at the main inlet for alkylene oxide and at the outlets of any previously ending optionally present insert tubes or double tubes. This reactor design permits that the alkylene oxide addition is self-portioned because the distribution of the quantities of alkylene oxide supplied to the reaction mass at the different supply points in the reaction space or gap is defined by the ratio between the cross section of the insert tube of smallest diameter and the annular cross sections between each of the insert tubes and its neighboring larger insert tube or, finally, the reaction tube itself, in case of a tubular reactor, or by the ratio between the annular cross section of the inserted double tubes and the area corresponding to the sum of all annular cross sections between inserted double tubes, the annular cross section between the inner boundary of the annular gap and the insert double tube of smallest inner diameter and the annular cross section between the insert double tube of largest diameter and the outer boundary of the annular gap of the reactor. It is therefore sufficient to select insert tubes or double tubes of suitably selected dimensions for controlling the alkylene oxide addition to the reactor, so that expensive mass flow controllers for the alkylene oxide at each entry point are not necessary and only one is required for control of the overall quantity of alkylene oxide supplied to the reactor. The distribution of alkylene oxide to the further locations in the reaction space or gap with the inserted tube(s) or double tube(s) according to the invention permits that the supply of alkylene oxide can be performed with a single pump delivering the liquid alkylene oxide to the main inlet for alkylene oxide in the reactor head.

The catalyzed raw materials and, optionally, the alkylene oxide can be preheated in heat exchangers before entering the reactor, so that the entire reactor volume is used for the reaction only (and not for preheating). Suitable preheating temperatures for the catalyzed raw material range e.g. from 100 to 180° C., for the alkylene oxides e.g. from 20 to 60° C.

On the other hand, the liquid alkylene oxide which flows through an insert tube or double tube is preheated in any case on its way through these tubes or double tubes, which are located in the reaction zone, so that the further reaction of the already partially alkoxylated and thus less reactive material with the alkylene oxide is improved in a simple way. Simultaneously, the colder alkylene oxide in the insert tubes supports the removal of the reaction heat from the reaction mixture.

Due to a rather turbulent stream in the reaction space or gap the alkylene oxide, when supplied according to the invention in liquid form, is normally mixed with the catalyzed raw material immediately upon contact therewith.

In a particularly preferred embodiment of the process according to the present invention ring slit nozzles are used to feed the liquid organic substance into the interior of the reaction space of said tubular reactor (a) or to the interior of the reaction gap of said annular gap reactor (b). This technique further improves the efficiency and the speed of the intermixture of the liquid catalyzed raw material injected into the reaction space or gap with the alkylene oxide significantly.

Additionally, fixed (or static, what is used synonymously herein) mixing elements are preferably used for supporting and improving and further accelerating the mixing of the alkylene oxide with the raw material or partially reacted mass at the inlets for the alkylene oxide to the reaction space or gap or along the way of the reaction mass towards the outlet of the reactor. Static mixers are known and in use since about 50 years and are devices for mixing two fluid materials, most commonly, liquids. The device consists of mixing elements contained in a housing, e.g. a tube. These can vary in size from about 6 mm to several centimeters diameter. Static mixer elements consist of a series of baffles that are e.g. made from metal. Typical materials of construction for the static mixer components include e.g. stainless steel. E.g. two streams of liquids are delivered into the static mixer system. As these streams move through the mixer and the non-moving fixed mixing elements continuously blend the materials. Mixing is dependent on variables like the fluid properties, tube inner diameter, the number of elements, and the design of the mixing elements. Static mixer systems are also commercially available, e.g. from Robbins & Myers, Inc or Sulzer Chemtech Ltd (e.g. Sulzer SMX mixer, cf. Sulzer Technical Review 2+3/2009, 23-25). Static mixing elements are, according to the invention, preferably located at said second location, where the catalyzed raw material is injected into the reaction space or gap. Optionally, one or more further static mixing element(s) are located between said second location and at the mentioned third location in the reaction space or reaction gap, where the second part of liquid alkylene oxide is fed into the reactor for supporting the intermixture and reaction of the liquid alkylene oxide with liquid catalyzed raw material. Furthermore, one or more static mixing element(s) may be located at said third and/or downstream of said third location in the reaction space or reaction gap for supporting the intermixture of the liquid alkylene oxide with the liquid reaction mixture formed between said second and third location and/or at or downstream of the optional further locations in the reactor, where further liquid alkylene oxide is added to the reaction mixture.

The length of the insert tubes or double tubes defines the degree of reaction achieved during the single reaction zones, i.e. the shorter an insert tube or double tube is in general, the smaller is the degree of reaction taking place in the zone of the reaction space or gap of the reactor which is traversed by the respective tube or double tube and the larger is the residual conversion after said tube or double tube. Preferred reference values for the total length of the reactor space or gap range from about 2 to about 25 meters, preferably from about 5 to 10 meters, but can be different, of course, in certain cases. Preferred reference values for the length of the insert tubes or double tubes range from about 4 to 90 percent of the total length of the reaction space or gap.

Preferably, the reactor is furthermore equipped with two or more, more preferably three, separate tempering, i.e. cooling or heating jackets, which are consecutively in longitudinal direction of the reactor fitted to the reaction tube(s) of said tubular reactor (a) or to the outer and inner tube of the annular-gap reactor (b), the first one of said tempering jackets e.g. being partially or completely located at a position between said second and third location, the second one being located directly after said first tempering jacket and partially or completely after said third location and the optional third and further tempering jackets following consecutively after said second tempering jacket. In this way it is possible to control the temperature of the reaction mixture independently by liquid cooling or heating media of a suitable temperature present in said two, or optionally three or more separate tempering jackets in a way to avoid any local overheating of the reaction mixture and, on the other hand, to achieve a reaction of the alkylene oxide which is as complete as possible. Preferably, the temperature of the cooling/heating medium in the different sections is suitably adjusted to maintain the temperature of the reaction mixture in the reactor at the preferred level for this reaction, i.e. at 140-250° C., more preferably at 170-220° C. As indicated, it can be necessary to either heat the reaction mixture or to cool it in the different tempering zones.

In a further preferred embodiment of the process according to the present invention, the reaction mixture passes through an additional post reaction zone or space before leaving the reactor, which is located after the reaction tubes in case of a tubular reactor or after said annular reaction gap in case of an annular gap reactor (b) in a zone of the reactor following the main reaction zone, where the annular gap has preferably a larger inside width than said main reaction gap. The presence of a post reaction zone can significantly improve the final conversion rate of the alkylene oxide, so that end products with a residual content of unreacted alkylene oxide below e.g. 5 ppm or even below 1 ppm or less can be readily achieved. The post reaction space has preferably a volume of 0.5-5% of total volume of the reactor input (alkylene oxide+organic raw material). In case of a tubular reactor, one can consider the length of the main reaction zone to correspond to the distance between the location of the inlet for the liquid catalyzed raw material to the reaction space and the reaction tube ends. In case of an annular gap reactor the length of the main reaction zone can be considered to correspond to the distance between the location of the inlet for the liquid catalyzed raw material to the reaction gap and the begin of the zone of increased inside width of the annular gap when the post reaction zone has increased inside width. When the inside width of the annular gap is not increased in the post reaction zone, so that the main reaction zone invisibly switches over to the post reaction zone, the length of the main reaction zone can, for the purposes of the present invention, be considered to correspond to the distance between the location of the inlet for the liquid catalyzed raw material to the reaction gap and the end of the—in direction to the outlet of the reactor-last of the aforementioned tempering jackets mounted to the reactor.

A particular preferred embodiment of the process according to the present invention is performed in a reactor selected from (a) a tubular reactor comprising at least one reaction tube providing a reaction space inside of said tube, and
(b) an annular-gap reactor comprising an outer tube and an inner tube, longitudinally inserted into said outer tube, which form an annular reaction gap extending between the inner surface of the outer tube, which forms the outer boundary of the reaction gap, and the outer surface of the inner tube, which forms the inner boundary of the reaction gap, and (1) the supply of liquid alkylene oxide to the reactor is controlled by a single mass flow controller, the liquid alkylene oxide is fed to said reactor (a) or (b) via a single inlet socket which is connected with a source of liquid alkylene oxide via said mass flow controller and the alkylene oxide is split before entering the reaction space or gap into a first and a second part,
(2) said first part of alkylene oxide enters the reaction space or gap of said reactor (a) or (b) at a first location,
(3) the liquid organic substance is supplied to the interior of the reaction space of said tubular reactor (a) via a ring slit nozzle for feeding said liquid substance to the interior of the at least one reaction tube of the tubular reactor (a) and mixing it with the alkylene oxide, which is located in each of said reaction tubes at a second location at or downstream of said first location of the reaction space, or via two ring slit nozzles for feeding said liquid substance to the interior of the reaction gap of said annular gap reactor (b) and mixing it with the alkylene oxide, one ring slit nozzle being located in said outer tube and the other in said inner tube, which form the boundaries of the reaction gap, at a second location at or downstream of said first location of the reaction gap and is intermingled with the liquid alkylene oxide to form a liquid reaction mixture, which moves downstream towards the end of the reactor,
(4) the liquid alkylene oxide enters the reactor at said first location and over the entire-cross sectional area of the reaction space or gap at said location,
(5) said second part of alkylene oxide is split off at said first location or upstream thereof and is channeled from said first location to a third location in the reaction space or gap, through a tube in case of a tube reactor (a), or through a double tube, respectively, in case of an annular gap reactor (b), which tube or double tube is inserted into the reaction space or gap, extends from said first location to said third location of the reactor space or gap, respectively, and has a diameter being smaller than the inner diameter of said reaction tube or outer boundary of said reaction gap, thus leaving a reaction space between the outer surface of said tube or double tube, respectively, on one side, and the inner surface of the reaction tube or the outer boundary of the reaction gap, respectively, on the other side,
(6) said third location is located downstream of said second location in flow direction of the reactor charge,
(7) said second part of liquid alkylene oxide enters the reaction space or gap of the reactor at said third location and is intermingled with said liquid reaction mixture and reacts with it on its way downstream towards the end of the reactor, where it leaves the reactor through an outlet for the reaction product, and
(8) the inner pressure of the reactor is kept at a pressure level where alkylene oxide entering the reactor does not vaporize, in particular at about 20 to 70 bar.

Further to the aforementioned process characteristics,
(9) the temperature of the reaction mixture is controlled in said particular preferred embodiment of the process according to the present invention by conveying liquid tempering media of suitable temperature through two or three separate tempering jackets, which are consecutively in longitudinal direction of the reactor fitted to the reaction tube(s) of said tubular reactor (a) or to the outer and inner tube of the annular-gap reactor (b), the first one of said tempering jackets being partially or completely located at a position between said second and third location, the second one being located directly after said first tempering jacket and partially or completely after said third location and the optional third tempering jacket follows consecutively after said second tempering jacket,

(10) the intermixture of the liquid alkylene oxide with said liquid substance is additionally supported by one or more static mixing element(s) located at said second location and, optionally, by one or more further static mixing element(s) located between said second location and at said third location in the reaction space or reaction gap and/or the intermixture of the liquid alkylene oxide with said the liquid reaction mixture formed between said second and third location in the reactor is further supported by one or more static mixing element(s) located at said third and/or downstream of said third location in the reaction space or reaction gap,

(11) the temperature of the reaction mixture in the reactor is maintained between 140 and 250° C., preferably 170-220° C.,

(12) the reaction mixture passes through an additional post reaction space before leaving the reactor, which is located after the reaction tubes in case of a tubular reactor or after said annular reaction gap in case of an annular gap reactor (b) in a zone of the reactor following the main reaction gap, where the annular gap has a larger inside width than said main reaction gap and

(13) the residual alkylene oxide content of the material leaving the reactor is preferably below 1 ppm.

A preferred embodiment of the present invention uses a single insert tube or double tube and the cross-sectional area of said single tube or double tube is from 50 to 5% of the sum of said cross-sectional area and the cross-sectional area of the reaction space or gap at the first location.

Diverse organic materials can advantageously be reacted with alkylene oxide according to the process of the present invention. In particular, primary straight chain or branched fatty alcohols, e.g. straight chain native alcohols made from natural oils or fats like e.g. fatty alcohols marketed under the name Lorol (e.g. Lorol C12-14) as well as synthetic Ziegler alcohols, in particular straight chain alcohols made from ethylene like the C12-16 fatty alcohol marketed as Condea Alfol 12-16, and oxo-alcohols (alcohols that are prepared by adding carbon monoxide (CO) and hydrogen, usually combined together as synthesis gas, to an olefin to obtain an aldehyde using the hydroformylation reaction and then hydrogenating the aldehyde to obtain the alcohol, e.g. n-butanol, 2-ethylhexanol or isononylalkohol) can be alkoxylated. Unsaturated fatty alcohols can also be alkoxylated, such as tallow fatty alcohol. More rarely used are secondary alcohols. Furthermore, n-alkyl phenols or alkyl phenols with branched alkyl chains such as octyl phenol, nonyl phenol, tributyl phenol, fatty acids, fatty acid alkanol amides, fatty amines, hydroxy fatty acids containing neutral oils such as ricinus oil and fatty acid esters from poly hydroxy compounds can be used as starting material.

Manufacturing the catalyzed raw material is preferably performed continuously. A part of the liquid chemical compounds for alkoxylation is premixed with an aqueous alkali metal hydroxide solution or an alcoholic solution of an alkali metal alcoholate, preferably in a thin film evaporator. The water from the alkali metal hydroxide solution and the reaction water are removed at elevated temperatures under vacuum. Similarly, the alcohol from the alkali alcoholate solution and further alcohol generated during the alcoholate formation is removed at higher temperatures under vacuum to below 0.05 weight %. Therefore the formation of poly glycols or alkyl poly glycols is minimized. This premix is then mixed with the remaining of the liquid chemical compounds in a way that the catalyzed raw material contains about 0.1 to 1 mol-% of the catalyst. The catalyzed raw material can immediately be fed into the reactor and reacted with the alkylene oxide in order to avoid a temperature loss of said material.

Preferred alkylene oxides for the present invention are ethylene oxide, propylene oxide and mixtures thereof.

In a particular embodiment of the present invention alkyl phenols reacted with up to 9 moles ethylene oxide (EO) and more, e.g. 3 to 9 moles, tributyl phenol e.g. with about 7 moles ethylene oxide, and primary native and synthetic fatty alcohols e.g. with 2-3 mole ethylene oxide are produced, products which are frequently used in industrial practice for a further sulfonation. The latter product represents the main quantity of ethoxylated substances worldwide and is produced by subsequent sulfonation with $SO_3$ to the ether sulfates (lauryl ether sulphates), LES $C_{12-14}$ with 2-3 Mol EO, alcohol ether sulphates, AES $C_{12-14/15}$ with 2-3 Mol. EO. These ether sulfates are used e.g. in household products, personal care products, cosmetics, liquid dish wash detergents, shampoos and bubble bath. The total annual worldwide production of such sulfonated anionic surfactants is about 4,000,000 tons.

Furthermore, e.g. dimethyl fatty alkyl amine hydrochlorides can be alkoxylated, for example with 0.9 Mol ethylene oxide. In this case it is especially easy to perform the alkoxylation according to the process of the present invention, since the lower the molar amount of ethylene oxide used for the alkoxylation, the lower is the heat of reaction. It is clear, of course, that a suitable material of construction needs to be selected for the reactor which is resistant to the chloride ions of the raw material.

The alkoxylation process according to the present invention generally results in alkoxylation products having a particular narrow molecular weight distribution on contrary to processes wherein semi batch reactors are used which result in products having a much wider range of molecular weight distribution.

Particularly preferred for the purposes of the present invention is the use of a tubular reactor because this design is in general mechanically more stable.

A further important embodiment of the present invention is the continuous alkoxylation of catalyzed raw material as described above in an annular gap reactor with a single inserted double tube. This reactor design causes a division of the liquid alkylene oxide into three streams, one entering the reaction gap at the first location via the annular cross section I, extending from the outer surface of said inserted double tube to the outer boundary of the reaction gap, a second entering the reaction gap also at said first location via the annular cross section II, extending from the inner boundary of the reaction gap to the inner surface of an inserted double tube, and a third stream channeled through the insert double tube and entering the reaction gap at the outlet ending of said double tube.

For the purposes of the present invention this two-stage annular gap reactor is preferably dimensioned such that 10 to 90 percent of the alkylene oxide enter the reaction gap via the cross sections I and II and the balance to 100 percent through the insert double tube.

More preferably the insert double tube of the aforementioned gap reactor has a length of 4-70 percent of the length of the entire reaction gap of the reactor.

Figure 1B:
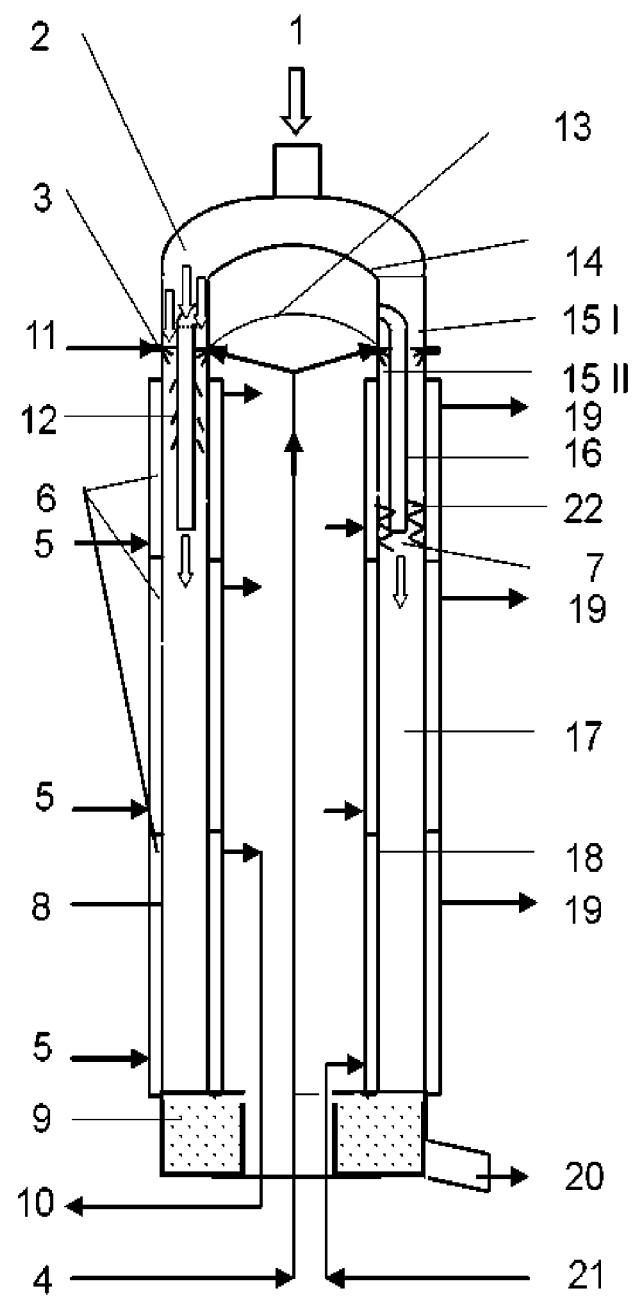
FIG. 1B is a representation of a two-stage annular gap reactor with a post reaction zone wherein the annular gap has a larger inside width than said main reaction gap of the reactor.
Figure 2:
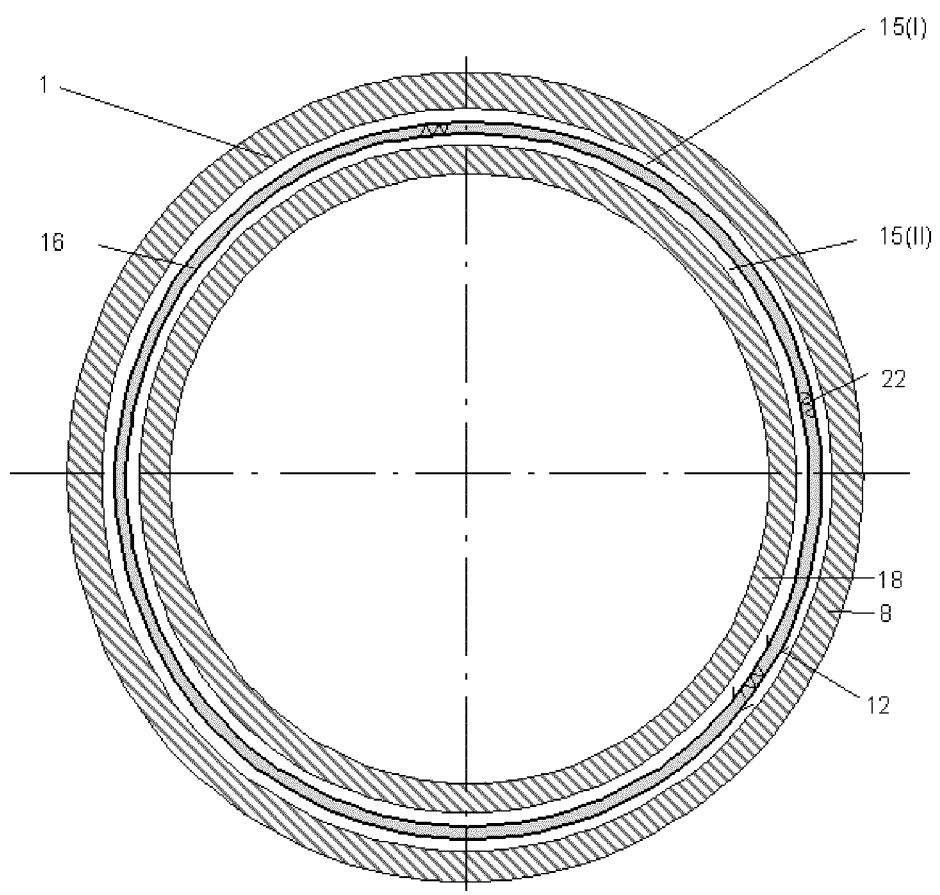
FIG. 2 is a representation of the principle of the invention for a two stage annular-gap reactor, top view.

The design of this device is schematically shown in FIGS. 1A, 1B and 2 (top view). An annular gap reactor is preferably 5 to 20 m long, more preferably about 5 to 15 m, the total inner width of the reaction gap is preferably between 5 and 15 mm. In an annular gap reactor consisting of two concentric jacketed tubes, an inner reactor tube (14,18) and an outer reactor tube (8) with an insert double tube (16) in the reaction gap (reaction chamber) (15, 17). The jackets are designed with cooling/heating areas divided in three sections each. The liquid catalyzed raw material is supplied uniformly into the interior of the reaction gap through a ring-shaped distribution slit in the inner (4) and outer tube (11) (ring slit nozzles) (3 and 13). Preheated liquid alkylene oxide is applied over the reactor head (1), so that one part of alkylene oxide is fed directly via the two annular cross sections of the reaction gap (15I and 15II) at the first junction point defined by the outer wall of the inserted double tube and the inner wall of outer reaction tube and the outer wall of the inner reaction tube and the inner wall of the inserted double tube. The double tube is preferably inside-stabilized (22). The remaining alkylene oxide quantity enters the inserted double tube over a third annular cross section which forms the entrance of said double tube (16) and is channeled through said double tube to a lower point in the reaction gap (7) depending on the insert distance of the double tube in the reaction gap.

Preferably, the annular cross-sectional area of the inserted double tube at said first location is 90 to 10% of the sum of said cross-sectional area, the annular cross sectional area (I), extending from the outer surface of said inserted double tube to the outer boundary of the reaction gap, and the annular cross section (II), extending from the inner boundary of the reaction gap to the inner surface of an inserted double tube.

The alkylene oxide distribution system (2) is self proportioning corresponding to the two previously mentioned annular cross sections over which the alkylene oxide enters the reaction gap at the first junction point and the annular cross section at the entrance-side of the insert double tube. The second feeding point for alkylene oxide to the reaction gap is defined by the length of the inserted double tube (16). The entrance of the inserted double tube annular gap is located above the distribution slits (ring slit nozzles) for the liquid catalyzed raw material (3 and 13).

The turbulence at the alkylene oxide inlet points causes the liquid raw material charged over the inner (13) and outer (11) distribution slits (ring slit nozzles) to be promptly mixed homogenously with the alkylene oxide on its way down stream. The efficiency of the mixing is preferably improved by mixing elements (12) fixed within the reaction zone.

The three sections of the heat exchange jackets (6) of the inner and outer tube forming the reaction gap allow the control of the temperature of the process as required. The tempering (cooling or heating) medium is applied via inlets (5) and (21). The outlet of the medium occurs via manifolds (10, 19). The reaction mix (20) leaves the reaction area (17) and is intermediately disposed in the residence chamber (9) where a post reaction follows (post reaction space). This product mix leaves the residence chamber and is led into a cyclone for removal of gaseous impurities of the raw material (hydrocarbons, aldehydes, $CO_2$) and other substances, which pollute the final product (alkylene oxide, dioxolane, dioxane). Thereafter, the final product is cooled and neutralized if necessary with for example lactic acid. A final filtration of this neutralized product may follow.

FIG. 1B shows an annular gap reactor as shown in FIG. 1A, wherein the inner boundary of the reaction gap in the post reaction zone of the reactor is formed by an inner tube having a smaller diameter than the tube forming the inner boundary of the main reaction gap resulting in a post reaction space (9) which has a larger inside width than said main reaction gap. The increased volume of the post reaction zone of the reactor contributes to decrease in reactor length without reducing the total residence time of the reaction mixture in the reactor and thus increasing the residual alkylene oxide content of the reaction product.

Another embodiment of the invention is the continuous alkoxylation of catalyzed raw material as described above in a special multi tube reactor. This multi tube reactor contains one smaller insert tube in each of its multiple reaction tubes. The liquid alkylene oxide is divided by virtue of the inserts into two streams. Preferably, the insert tubes of a multi tube reactor have a length of about 10 to 50 percent of the length of said reaction tubes.

Figure 3:
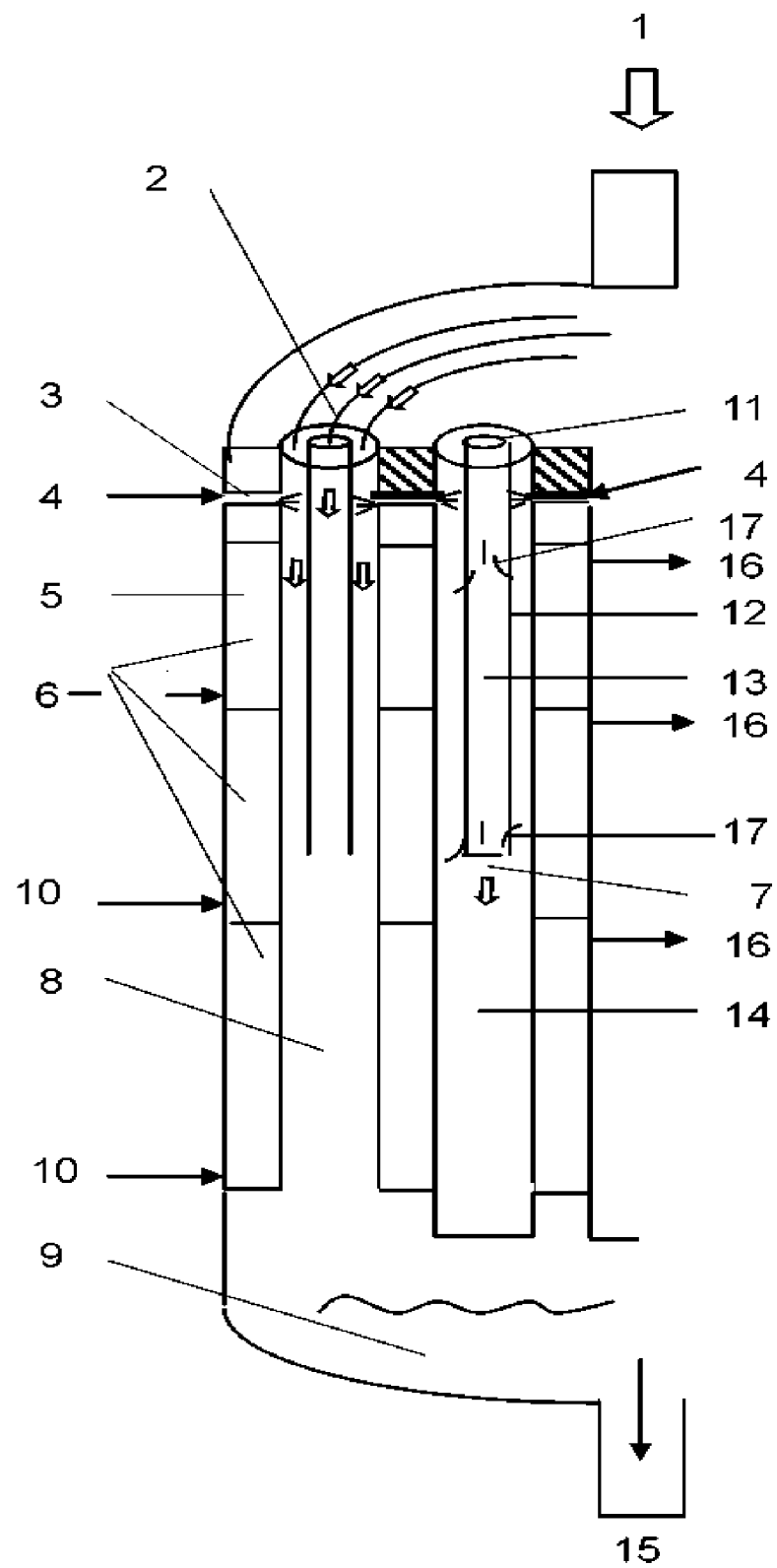
FIG. 3 is a representation of the principle of the invention for a two-stage multi-tube reactor with mixing elements.
Figure 4:
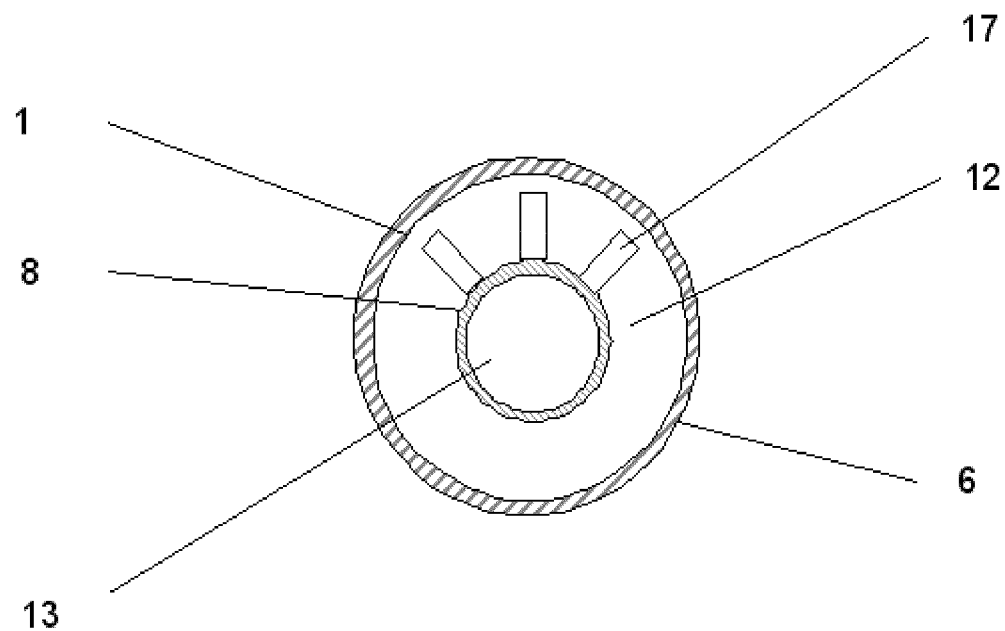
FIG. 4 is a representation of the principle of the invention for a two stage (multi) tube reactor, top view.

An example design of this device is shown in more detail in FIGS. 3 and 4.

The multi tube reactor for performing the alkoxylation consists, similar to a tubular heat exchanger, of a multitude of reaction tubes (8) and insert tubes (13) in the inner space at the top of each reactor tube. Each insert tube is preferably centered within the reaction tubes. The reactor is preferably 5 to 20 m long, more preferably about 5 to 15 m, in particular 5 to 10 m, the reaction tubes have preferably a diameter of 10 to 25 mm. The heat exchange-jacket or shell (5) with e.g. three different sections (6) allows controlling the temperature as required by the process. The liquid catalyzed raw material (4) is supplied uniformly via a special raw material distribution (3), in particular via ring slit nozzles located in the reaction tubes. The alkylene oxide is supplied to the reactor head (1) so that one part goes over the distribution chamber directly to the first alkylene oxide junction point of the reaction tube inlets (11) to a first reaction zone (12) in the reaction tubes and the remaining quantity goes over the inserted smaller tubes (13) to a lower second alkylene oxide junction point (7) and to a second reaction zone (14) positioned lower in the reactor. The self proportioning of the total supplied alkylene oxide occurs at location (2) corresponding to the cross section of the inserted tube (13) in relation to the annular area represented by the cross section of the reactor tube minus the cross section of the inserted tube.

The streaming speed of alkylene ethylene oxide and—preferably present—fixed mixing elements (17) in the annular gap formed by the tubes and the insert tubes cause immediate homogeneous mixing with the raw material supplied from the raw material distribution device (3). The three heat exchange sections allow individual control of the temperature. The cooling or heating medium, respectively, is supplied via the manifold (10). The medium outlet occurs through line (16). The reaction mix (15) from the second zone (14) of the reaction space flows through a final reaction chamber (9) for post reaction. A final degassing from remaining inert gases of the raw material like e.g. acetaldehyde or $CO_2$, and from substances formed in the final product during the reaction, e.g. dioxane or dioxolanes, in a cyclone follows. Then, the final product is cooled and neutralized if necessary with lactic acid. If desired, the neutralized product can be filtered.

With this method, a reaction in two steps is realized, such as in a cascade. In the first step only a part of the stoichiometrically desired liquid alkylene oxide is supplied, in order to limit the amount of reacting material and thus the heat of reaction and the resulting temperature in the reactor, because only a partial reaction takes place, when the reaction starts with a smaller quantity of alkylene oxide than necessary for the final product (e.g. 70 percent, corresponding to a distribution of the amount of alkylene oxide of 70:30 between the two process steps). The development of reaction heat is therefore significantly smaller, so that a strong temperature increase in the first section of the reactor is avoided, and the reaction heat can be better removed by the cooling jacket. Due to this kind of processing, the exothermic reaction and the temperature behavior of an alkoxylation are much easier to control.

In case of annular gap reactors, in which the organic raw material is supplied via slits (ring slit nozzles) into the gap between the inner wall of the outer tube and the outer wall of the inner tube, a double tube is inserted in the annular gap (insert double tube) through which a part of the alkylene oxide is provided to the reaction gap further downstream and added to the mixture which has already partially been alkoxylated upstream in the reactor. In this way, a self-controlled proportioning of the total quantity of alkylene oxide intended for reaction with the catalyzed raw material into two parts is realized, corresponding to the relation between the sum of the partial annular cross-sections 15I and 15II (see FIG. 2) of the reaction gap and the annular cross-section of the insert double tube.

Depending on the length of the inserted double tube the conversion degree in the first part of the reactor and the residual conversion in the second zone can be adjusted.

A quite similar self-controlled alkylene oxide proportioning occurs in multi tube reactors according to the present invention. In each reaction tube of the multi tube reactor a smaller insert tube is inserted. A first part of the total quantity of alkylene oxide intended for reaction is supplied on top of each reaction tube via the annular space between reaction and insert tube and is directly brought into contact with the catalyzed raw material of the reaction tubes. The second portion of alkylene oxide reacts downstream after the end of the insert tubes in each of the reaction tubes with the already partially alkoxylated reaction product. The quantities of alkylene oxide added at the first supply location for alkylene oxide in each reaction tube and at the end of each insert tube are determined by the cross sections of the insert tube and the annular cross-section between the outer diameter of the insert tube and the inner diameter of the associated reaction tube. In this way, the reaction degree between first and second alkoxylation step is defined. Again, the conversion degree in the first part of the reactor and the residual conversion in the second zone can be adjusted by variation of the length of the insert tubes.

The length of the insert tube(s) in (multi) tube reactors or the insert double tube in annular gap reactors can e.g. range from 20 to 70 percent of the length of the reactor space or gap.

The insert tubes and insert double tubes are simple in design, and can be easily affixed to the reactors and centered in the reaction space or gap by spacers. These spacers also cause a turbulence and a mixing effect in the reaction material.

Moreover, due to the small reaction volume and the minimized portion of alkylene oxide in the reaction chamber, a previous inertization with nitrogen for safety reasons is not necessary.

Figure 5:
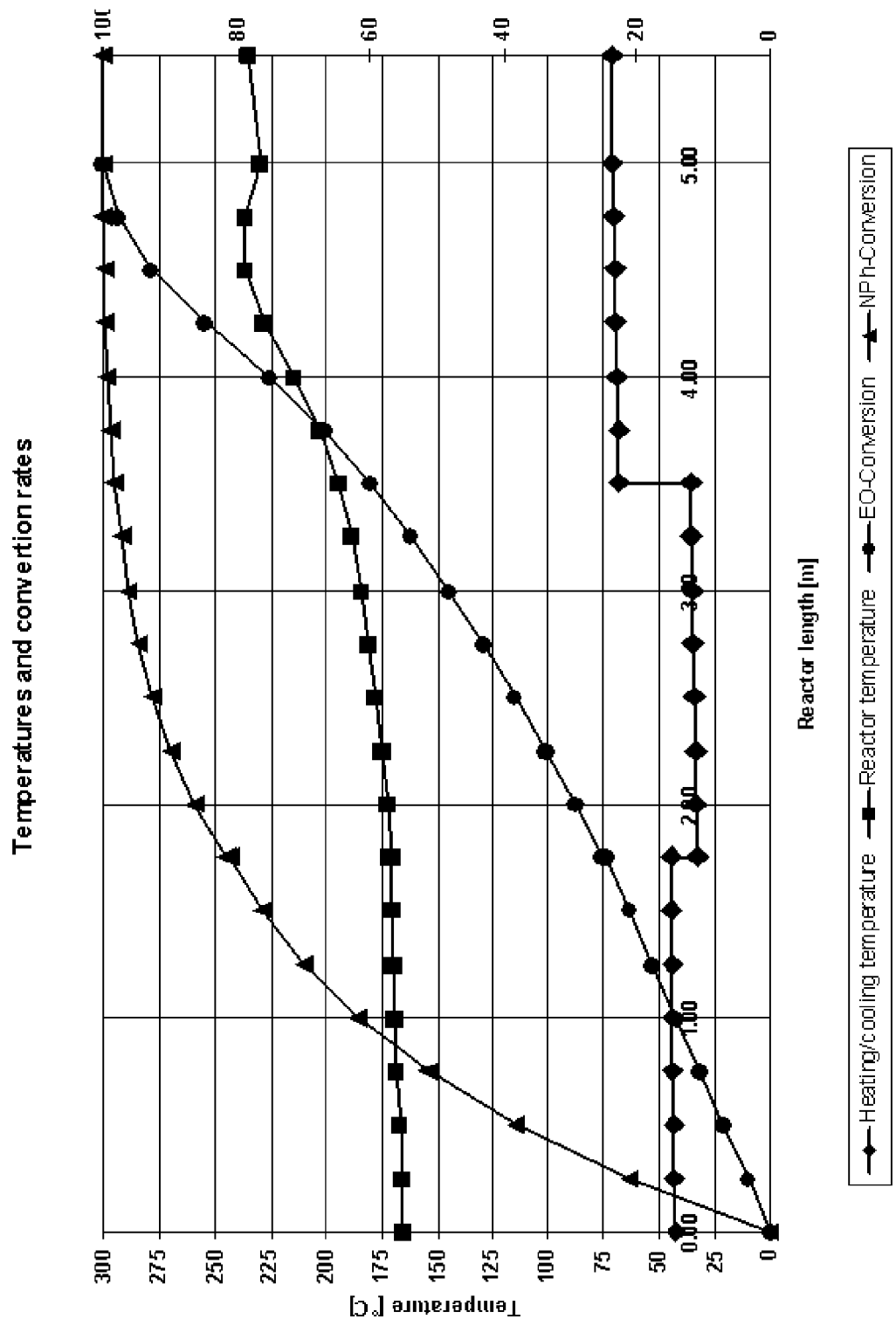
FIG. 5 shows the temperature progress in the reaction mixture and the cooling/heating temperature in the two stage annular gap reactor of Example 1.
Figure 6:
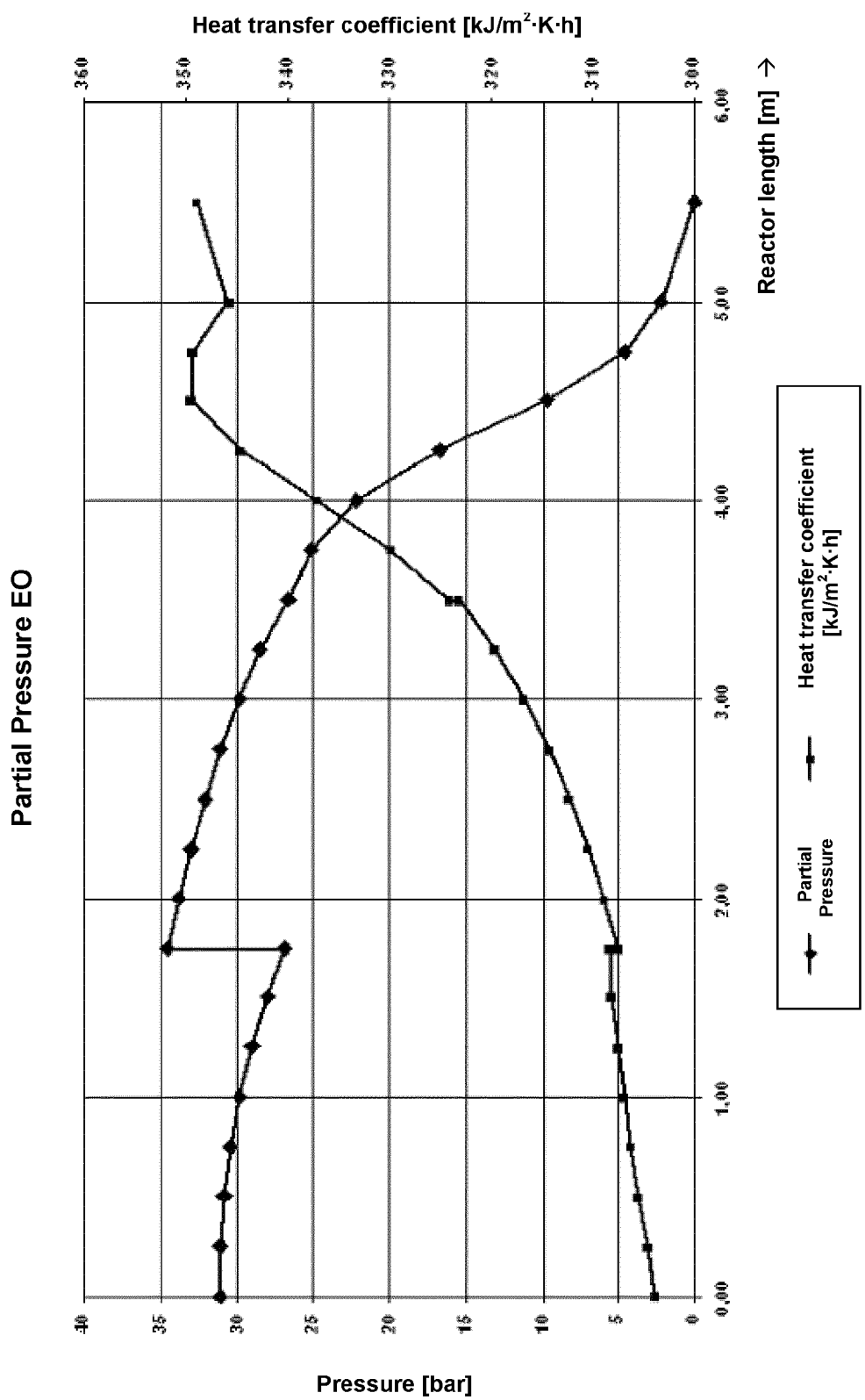
FIG. 6 shows the partial pressure progress in the two stage annular gap reactor of Example 1.

The following Examples are provided for further illustration of the invention and shall not limit the scope of the invention. In particular, designing and sizing of the apparatus for different capacities is easily possible for persons of ordinary skill in the art. The reaction progress is shown in FIG. 5 (capacity, temperature development in the reaction mixture, cooling/heating temperatures). The ethylene oxide partial pressure development is shown in FIG. 6.

EXAMPLES

Example 1

Reaction of n-nonyl phenol with 7 mole ethylene oxide in a 5 inch annular gap reactor of 5 m length with inserted double tube, with static mixing elements downstream the raw material input and at the second ethylene oxide input, with a length of 1.750 m (35% of the total reactor length) according to the invention with a capacity of 250.8 kg/h that corresponds to 2008 tons/year.

An annular gap reactor has a geometry according to FIGS. 1 and 2, with an inner diameter of the outer tube of 5 inches=127.0 mm and an outer diameter of the inner tube of 114.0 mm and a reactor length of 5.000 m, with an annual gap width of 6.5 mm (annular space volume of 11.31 liters) and a supply for the liquid catalyzed raw material via a ring slit nozzle in the inner wall of the outer tube and another one in the outer wall of the inner tube. Both concentric tubes are jacketed tubes with three cooling or heating sections (see FIGS. 1A/B), whereby the upper jacket section takes 35% of the entire jacket length, the middle jacket also 35% and the lower 30%. The annular gap (annular space) contains a thin-walled insert double tube. The wall thickness of the reactor is 10 mm (see FIG. 2), the gap of the cooling/heating zone amounts to 6 mm and the volume of the post reactor amounts to 0.02 $m^3$. The wall thickness of the insert double tube (inner and outer tube shell) amounts to 0.5 mm, the outer diameter=122.67 mm, the inner diameter=118.33 mm, the distance from the outer and inner jacketed tube to the walls of the insert double tube amounts to (127−122.67)/2=2.17 mm and (118.33−114)/2=2.17 mm, respectively (see FIG. 1), the length of the insert double tube is 1.75 m (=35% of the total reactor length). The incorporated double tube diameters were dimensioned in this case so that the ethylene oxide is supplied about 82.25% through the two cross sections between outer and inner reactor tube and finally 17.75% through the incorporated double tube cross section.

For manufacturing the catalyst, a part of the total raw material n-nonyl phenol (MW=220) of 7.15 kg/h=0.0325 kmol/h and 0.38 kg/h of 50% caustic soda solution corresponding to 0.19 kg/h 100% caustic soda=0.0048 kmol/h=14.64 mol % appropriate to the n-nonyl phenol part are supplied after pre-mixing at a temperature of approx. 50° C. into a thin film evaporator (TFE) with an evaporator surface of 0.125 $m^2$. The jacket temperature is adjusted with pressure reduced steam to 150° C.=approx. 4 bar (pressure controlled). The water quantity from the caustic soda solution and the reaction water (total approx. 0.28 kg/h) that is to be distilled off is released by a vacuum pump system with approx. 30 mbar absolute. The formed sodium-n-nonyl phenolate with a rest water content of <0.05% is taken out of the evacuated TFE by a special pump and fed through a self cleaning slit filter for removing impurities. After this procedure it is mixed in a static mixer with 97.36 kg/h=0.4425 kmol/h fresh n-nonyl phenol (this mixture contains then 1 mol % sodium-n-nonyl phenolate as catalyst).

In the annular gap reactor with inserted double tube according to the invention the pressurized cooling/hot water pre run temperature in the upper jacket is adjusted to 35° C. and the water loop quantity is set to 5 $m^3$/h. The inlet temperature is kept constant by a "split range" automatic controller by monitored feeding of pressure steam, in case of preheating, and water, in case of cooling, into the pressure loop. In the middle jacket section the water loop quantity is adjusted to 5 $m^3$/h and 55° C. and the same in the lower jacket.

The mixture of fresh n-nonyl phenol and the catalyzed n-nonyl phenol (the mixture now contains 0.6 mol % catalyst) is pumped by a special TFE discharge pump over a heat exchanger with a set temperature of 165° C. and over both distribution slits (ring slit nozzles) with a quantity in proportion to the gap of 104.62 kg/h n-nonyl phenol, including formed alcoholate as catalyst, controlled by mass flow meter into the space between the inner and outer concentric jacketed tubes. Over a supply pipe on the reactor head 146.32 kg/h=3.3257 kmol/h ethylene oxide (n-nonyl phenol related to ethylene oxide=1 to 7.0) are fed with a high pressure pump. Through the inserted double tube (1.750 m=35% of the total reactor length from top) a quantity of 25.37 kg/h (=17.75%) of the ethylene oxide flows and the remaining quantity of the ethylene oxide of about 120.35 kg/h (=82.25%) flows through the cross sections (I+II) (see FIG. 2) of the annular gap. The proportionate ethylene oxide conversion in the 1st section of the reactor (35% of reactor length) should be 25%, 35% in the 2nd section (35% of the reactor length) and 40% in the 3rd section (30% of the reactor length).

The reaction mixture at a temperature of approx. 236° C. exits the ring chamber (approx. 0.02 m$^3$) via a pressure control valve (50 bar) into a cyclone for degassing (inert gas from ethylene oxide, formed by-products e.g. dioxane). The gases are discharged then with a water ring vacuum pump and led to combustion or to a scrubber. In the cyclone a small vacuum is maintained at approx. 700 mbar absolute. If necessary, stripping steam can also be introduced into the cyclone. Hence a better degassing will be achieved. Afterwards the end product is cooled to approx. 60° C. in a heat exchanger with a recycle loop to the cyclone.

For neutralization with lactic acid (0.54 kg/h) by a dynamic mixer, the reaction mix is pumped over a heat exchanger in a loop with approx. 5 m$^3$/h. The final product is discharged from the loop to the filtration or to the storage tank.

During start up of the alkoxylation reactor the procedure proceeds as follows: The annual gap reactor is first filled up with the concentrated, filtered catalyst mixture from the thin film evaporator and the fresh n-nonyl phenol mixed in a static mixer. The mixture containing 0.6 mol % catalyst is fed in the preset quantity per hour to the reactor after preheating to 165° C.

Immediately after achieving a low liquid level in the cyclone (level controlled) ethylene oxide, also in the preset quantity per hour, is pumped over the pre heater into the reactor. The pressure control valve in the reactor output line is adjusted to 50 bar (vapor pressure of ethylene oxide at 165° C. is approx. 50 bar). The temperature controllers for each section of the three heating/cooling loops of the reactor are adjusted to the required temperature.

Product Specification

Hydroxyl value (mg KOH/g): 106 calculated MW=528=7.0 mole EO
Color (visual): light yellow
Color (APHA): 20 max.
Density 50° C.: app. 1.04 g/cm$^3$
Pour point: 7° C.
Viscosity dynamic 50° C.: app. 65 mPas
Dioxane content (head space GC): max. 1 ppm
Ethylene oxide: max. 1 ppm
Polyglycol: 1%
Moisture (Karl Fischer): 0.05 weight %

Example 2

Reaction of n-nonyl phenol with 15 mole ethylene oxide in a 5 inch annular gap reactor of 5 m length with insert double tube, with static mixing elements downstream the raw material input and at the second ethylene oxide input, with a length of 1.750 m (35% of total reactor length) according to the invention with a capacity of 260 kg/h that corresponds to 2008 tons/year.

In comparison to Example 1 (7 mole ethylene oxide) the capacity is retained for the same reactor size. The reactor temperature is a little bit higher, since due to the higher ethylene oxide quantity (15 moles) the reaction heat increases. For the Example 2 the same annular gap reactor according to FIGS. 1 and 2 (dimensions as in Example 1) and the same thin film evaporator equipment as in Example 1 is used.

For manufacturing the catalyst a part of the total raw material (65 kg/h) n-nonyl phenol that means 4.45 kg/h=0.0202 kmol/h and 0.24 kg/h 50% NaOH solution corresponding to 0.12 kg/h 100% NaOH (caustic soda)=0.0030 kmol/h=14.64 mol % in relation to n-nonyl phenol, are both fed at 50° C. into a thin film evaporator (0.125 m$^2$) after pre-mixing. The thin film evaporator (TFE) is heated by 4 bar steam at approx. 150° C. (pressure controlled). The water quantities from caustic and the reaction water (in sum 0.17 kg/h) to be distilled off are exhausted by a water jet (30 mbar absolute). The sodium-n-nonyl phenolate with a residual water content of lower than 0.05% is taken out off the evacuated thin film evaporator by a gear pump and separated from impurities over a slit filter. Subsequently it is mixed in a static mixer with fresh n-nonyl phenol 60.55 kg/h corresponding to 0.2752 kmol/h (the blending then contains 0.6 mol % sodium-n-nonyl phenolate as catalyst).

The pressurized pre-run water temperature of cooling/heating in the upper reactor jacket section is fixed at 136° C., the water loop approx. at 5 m$^3$/h. The entrance temperature is controlled by "split range" controlling which holds the temperature by injecting steam or cooling water into the loop. The middle jacket is connected to a water loop at 5 m$^3$/h and 23° C. and the lower jacket is connected to a water loop at 5 m$^3$/h and 35° C.

The discharge gear pump from the thin film evaporator pumps the catalyzed (0.6 mol %) n-nonyl phenol (65.07 kg/h, mass flow meter) over a heat exchanger with a set temperature of 165° C. through the inner- and outer distribution slits (ring slit nozzles) equally into the corresponding reaction space. Over the reactor head, 195.00 kg/h liquid ethylene oxide (=2.0683 kmol/h) is charged by a pressure pump (proportion n-nonyl phenol to ethylene oxide is 1:15). Dimensions of the insert double tube: Length 70% of the total reactor length, which means 3.500 m. Through the annular cross section of the jacketed concentric inner and outer tube (diameters $d_i$=114 mm, $d_{out}$=127 mm) 82.25%=160.39 kg/h is charged. Through the cross section of the insert double tube (Example 1) the residual quantity of ethylene oxide, which means 43.61 kg/h=17.75% is charged (3.5 m). The proportionate ethylene oxide conversion in the 1st section of the reactor (35% of the reactor length) should be 15%, 35% in the 2nd section (35% of the reactor length) and 50% in the 3rd section (30% of the reactor length).

The reaction mix exits the ring chamber (0.02 m$^3$) controlled via a pressure resistance valve to be degassed from the inert gases from ethylene oxide and formed by-products such as dioxane. Afterwards cooling to 60° C. follows in a heat exchanger and a recycling loop to a cyclone.

For neutralizing with lactic acid (0.34 kg/h) the reaction mix is pumped over a dynamic mixer and following cooler in a loop (5 m$^3$/h). The final product from the neutralizer loop passes a filter and is discharged to the storage tanks.

Product Specification
Hydroxyl value (mg KOH/g): 63 calculated MW=880=15.0 mole EO
Color (visual): light yellow
Color (APHA): 20 max.
Density 50° C.: app. 1.07 g/cm$^3$
Pour point: 25° C.
Viscosity dynamic 50° C.: app. 80 mPas
Dioxane content (head space GC): max. 1 ppm
Ethylene oxide: max. 1 ppm
Polyglycol: 1%
Moisture (Karl Fischer): 0.05 weight %

Example 3

Preparation of n-nonyl phenol ethoxylate with 3 mole ethylene oxide in a 5 inch annular gap reactor of 5 m length with insert double tube, with static mixing elements downstream the raw material input and at the second ethylene oxide input, with a length of 1.750 m (35% of the total reactor length) according to the invention with a capacity of 704 kg/h, which corresponds to 5653 tons/year.

In comparison to Example 1 the throughput is raised above proportion due to the lower ethylene oxide part (3 mole) in the same reactor size, since the reaction heat is smaller.

For Example 3, the same annular gap reactor according to FIGS. 1 and 2 (dimensions as in Example 1 and the same thin film evaporator equipment as in Example 1) are used.

For catalyst manufacturing in Example 3, a part of the total raw material (440 kg/h) n-nonyl phenol that means 30.10 kg/h corresponding to 0.1368 kmol/h and 0.96 kg/h 50% NaOH solution equivalent to 0.480 kg/h 100% NaOH (caustic soda)=0.0120 kmol/h=8.78 mol % in relation to n-nonyl phenol, are both fed (after pre-mixing) at 50° C. into a thin film evaporator having an exchanger surface of 0.125 m$^2$. The thin film evaporator is heated by 6 bar steam (pressure controlled). The water quantities from caustic and reaction (0.7 kg/h) to be distilled off are exhausted by a water jet (30 mbar absolute). The consisted sodium-n-nonyl phenolate with a residual water content of lower than 0.05% is removed from the evacuated thin film evaporator by a gear pump and filtered from pollution over a rotating slit filter. Thereafter the catalyst is mixed in a static mixer with fresh n-nonyl phenol 409.90 kg/h=1.8632 kmol/h (the mixture then contains 0.6 mol % sodium-n-nonyl phenolate).

The water supply temperature of cooling/heating in the upper reactor jacket is fixed at 75° C., the water loop approx. at 5 m$^3$/h. The constant inlet temperature is controlled by "split range" controlling. The middle jacket admits a loop water quantity of 5 m$^3$/h and 75° C. and the lower jacket operates at 5 m$^3$/h and 75° C.

The discharge gear pump pumps the catalyzed (0.6 mol %) and fresh n-nonyl phenol (440.26 kg/h, by mass flow meter) from the thin film evaporator over a heat exchanger with a set temperature of 165° C. through the inner and outer distribution slits (ring slit nozzles) equally between the reactor walls. 264 kg/h liquid ethylene oxide=6.000 kmol/h is charged over the reactor head by a pressure pump (proportion n-nonyl phenol to ethylene oxide is 1:3). Dimensions of the insert double tube: Length 35% of the total reactor length means 1.750 m. Through the annular cross section of the jacketed concentric inner tube and outer tube (diameter $d_i$=114 mm, $d_{outer}$=127 mm) 82.25%=217.14 kg/h ethylene oxide is charged. Through the cross section of the insert double tube the residual quantity of ethylene oxide meaning 46.86 kg/h=17.75% is charged (1.75 m from first feed location). The proportionate ethylene oxide conversion in the first section of the reactor (35% of the reactor length) should be 20%, 40% in the 2nd section (35% of the reactor length) and 40% in the 3rd section (30% of the reactor length).

The reaction mix exits the ring chamber (0.02 m$^3$) controlled via a pressure resistance valve (adjusted pressure is 50 bar) and is degassed from the inert gases ethylene oxide and formed by-products such as dioxane. These gases are discharged under assistance of the water pump to combustion or a scrubber. Afterwards cooling to 60° C. follows in a heat exchanger and partial recycling to the cyclone.

For neutralizing with lactic acid (1.54 kg/h, 70% weight, molecular weight 90 g/mol) the reaction mix is pumped over a dynamic mixer and a following cooler in a loop (5 m$^3$/h). The final product from the neutralizer loop is led to storage after passing a filter.

Product Specification
Hydroxyl value (mg KOH/g): 159.4 calculated MW=352=3.0 mole EO
Color (visual): light yellow
Color (APHA): 20 max.
Dioxane content (head space GC): max. 1 ppm
Ethylene oxide: max. 1 ppm
Polyglycol: 1%
Moisture (Karl Fischer): 0.05 weight %

Example 4

Preparation of n-nonyl phenol ethoxylate with 3 mole ethylene oxide in a 5 inch annular gap reactor, with static mixing elements downstream the raw material input and at the second ethylene oxide input, 10 m long with insert double tube of 6 m length (60% of the total reactor length) and 0.6 mol % NaOH as catalyst according to the invention with a capacity of 704 kg/h, which corresponds to 5653 tons/year.

Compared to Example 3 with the same capacity, the reactor length is increased up to 10 m. The reaction is now spread over a greater length, so that the temperature maximum then decreases to 209° C.

For Example 4 the same annular gap reactor according to FIGS. 1 and 2 (dimensions as in Example 1) is used.

Catalyst manufacturing for Example 4 was performed analogous to Example 3.

Under assistance of a gear pump the catalyzed n-nonyl phenol with 0.6 mol % caustic soda is pumped over a heat exchanger with a set temperature of 165° C. and equally supplied over both distribution slits (ring slit nozzles) between the inner and outer reaction tube. Over the reactor head 264.00 kg/h=6.000 kmol/h ethylene oxide is charged by a pump (n-nonyl phenol to ethylene oxide is 1:3). Through the insert double tube cross section (60% of the total reactor length=6.000 m) 46.86 kg/h=17.75% and 217.14 kg/h=82.25% of the ethylene oxide is charged over the annular cross sections shaped by the inner and outer reaction tube. The proportionate ethylene oxide conversion in the 1$^{st}$ section of the reactor (35% of the reactor length) should be 40%, 40% in the 2nd section (35% of the reactor length) and 20% in the 3rd section (30% of the reactor length).

The reaction mix at 209° C. expands via a pressure control valve for degassing (inert gas from ethylene oxide and formed by-products e.g. dioxane) into a cyclone. After the degassing, cooling to 60° C. follows in a heat exchanger (recycling loop to cyclone).

The supply temperature of the pressurized (5 m$^3$/h) cooling/heating water loop in the upper jacket is adjusted to 73° C. Maintaining the inlet temperatures for the three jackets (reaction sections) is done via a "split range" controller responsible for steam and cooling water feeding. The middle jacket water loop runs at 5 m³/h and 116° C. The lower jacket water loop runs at 5 m³/h and 141° C.

The reaction mix is pumped in a loop for neutralization with lactic acid (0.23 kg/h) over a dynamic mixer and a 5 m³/h cooler. After exiting the loop, the end product is led to the storage after filtering.

Product Specification

Hydroxyl value (mg KOH/g): 159.4 calculated MW=352=3.0 mole EO

Color (APHA): 20 max.

Dioxane content (head space GC): max. 1 ppm

Ethylene oxide: max. 1 ppm

Polyglycol: 1%

Example 5

Preparation of a fatty alcohol $C_{12-14}$ ethoxylate with 2 mole ethylene oxide in a 5 inch annular gap reactor, with static mixing elements downstream the raw material input and at the second ethylene oxide input, 10 m long with insert double tube of 6 m length (60% of the total reactor length) according to the invention with a capacity of 852 kg/h, which corresponds to 6816 tons/year.

In Example 5a fatty alcohol $C_{12}$-$C_{14}$ is reacted with 2 mole of ethylene oxide. The output quantity in relation to Example 4 is increased using the same reactor size because due to the smaller ethylene oxide addition, less reaction heat is released. The temperature maximum then reaches 208° C. The average residence time in the reactor amounts to 55 seconds and 283 seconds in the post reactor (approx. 5 minutes total).

For Example 5, the same annular gap reactor in accordance with FIGS. 1 and 2 (dimensions as in Example 1) is used.

For the manufacturing of the catalyst a part of the total raw material (104.51 kg/h) fatty alcohol $C_{12-14}$ ($C_{12}$=65-71%, $C_{14}$=22-28%, $C_{16}$=4-8%, molar weight=196 (from hydroxyl value) that means 40.22 kg/h=0.2052 kmol/h and 1.44 kg/h 50% caustic soda solution=0.72 kg/h 100% NaOH=0.0180 kmol/h equivalent to 8.77 mol % related to the part fatty alcohol $C_{12-14}$, is fed after pre-mixing at a temperature of approx. 50° C. into a thin film evaporator (TFE) with an evaporator surface of 0.125 m². The jacket temperature of the TFE is adjusted by pressure steam to 150° C.=approx. 4 bar (pressure control). The water from the caustic soda solution and the reaction water (in sum approx. 1.04 kg/h) to be distilled off is exhausted by a water ring pump (vacuum approx. 30 mbar). The formed sodium $C_{12-14}$-fatty alcoholate with a rest water content of <0.05% is taken out of the vacuum by a special pump and passes a slit filter to separate impurities. Then the filtrate is mixed in a static mixer with fresh fatty alcohol $C_{12-14}$ 547.78 kg/h=2.705 kmol/h (the blending contains then 0.6 mol % sodium $C_{12-14}$ alcoholate as catalyst).

Under assistance of a gear pump the catalyzed fatty alcohol $C_{12-14}$ is led over a heat exchanger with a set temperature of 165° C. and is evenly led over the two distributor slits (ring slit nozzles) into the gap between the walls of the two concentric reaction tubes. Via a feed pipe at the reactor head 264.00 kg/h ethylene oxide (=6.000 kmol/h) (relationship fatty alcohol $C_{12-14}$ to ethylene oxide=1 to 2) is supplied by a high pressure pump. Through the inserted double tube (60% of the total length of the reactor=6.000 m) and over the above mentioned two cross sections of the annular gaps and the inserted double tube 82.25%=217.14 kg/h of the ethylene oxide are supplied between the annular gaps inside and outside of the inserted double tube. Over the inserted double tube the remaining quantity of ethylene oxide 46.86 kg/h=17.75% follows after 6.000 m from the reactor top. The proportionate ethylene oxide conversion achieves 40% in the $1^{st}$ part of the reactor (35% of the reactor length), 40% in the $2^{nd}$ part (35% of the reactor length) and 20% in the $3^{rd}$ (30% of the reactor length). The reaction mixture exits the reactor end at 208° C. and is then discharged from the ring chamber (approx. 0.02 m³) via a pressure control valve into a cyclone for degassing (inert gases from the EO, formed by-products e.g. dioxane). Afterwards cooling down to approx. 60° C. takes place in a heat exchanger by a recycle loop to the cyclone.

The pressurized heating/cooling water supply temperature in the upper jacket was adjusted to 85° C. by a loop quantity of 5 m³/h. The inlet temperatures for each section is kept constant by a "split range" automatically controlled feeding of steam or cooling water supply into the pressure water loop. In the middle jacket section the loop quantity is adjusted to 5 m³/h water at 129° C., and in the lower jacket the water loop quantity is adjusted to 5 m³/h and 153° C.

For neutralization with lactic acid (2.31 kg/h), the reaction mixture is pumped in a loop over a dynamic mixer and following cooler (loop quantity approx. 5 m³/h). From the neutralization loop, the final product is led to storage after filtering.

If the reaction mixture is supplied directly to a sulfation plant, neutralization with lactic acid is not necessary. The un-neutralized product can be stored temporarily in buffer vessel under a nitrogen blanket.

Example 6

Preparation of a fatty alcohol $C_{12-14}$ ethoxylate with 3 mole ethylene oxide in a 36 inch annular gap reactor, with static mixing elements downstream the raw material input and at the second ethylene oxide input, 10 m long with insert double tube of 6 m length (60% of the total reactor length) and 1 mol % catalyst according to the invention with a capacity of 4920 kg/h, which corresponds to 39360 tons/year.

Compared to Example 3, the ethoxylation is performed in a 36 inch annular gap reactor with a length of 10 m and a catalyst concentration of 1 mol % and a length of the inserted double tube of 6 m length (60% of the total length). Here the reactor is used for pre-heating of ethylene oxide and fatty alcohol. The feed temperature of ethylene oxide is 20° C. and the temperature of the fatty alcohol is 40° C.

The annular gap reactor according to FIGS. 1 and 2 consists of an outer tube with an inner diameter of 36 inches=914.4 mm and an inner tube with an outer diameter of 895.2 mm, and a reactor length of 10 m, with an annular width of 9.6 mm (annular space volume is 0.272 m³) and a raw material distributor slit (ring slit nozzle) in the inner and outer jacketed reaction tubes with three cooling/heating sections (see FIG. 1). The upper and middle jackets cover each 35% and the lower jacket covers 30% of the total reactor length. In the annular gap (annular space) a thin-walled double tube is incorporated. The wall thickness of the reactor amounts to 19 mm, the gap of the cooling/heating jackets is 8 mm and the volume of the post reactor amounts to 0.08 m³. The wall thickness of the insert double tube is 0.5 mm, the outer diameter is 908.0 mm, the inner diameter is 901.6 mm, and the slit width amounts to (908.0−901.60)/2=3.20 mm. The length of the insert double tube amounts to 6 m=60% of the total reactor length.

The diameter of the insert double tube is dimensioned such that 77.08% of the ethylene oxide is charged over the inner and outer annular gap and the remaining 22.92% over the insert double tube.

To manufacture the catalyst for Example 6, a part of the total raw material (2940.00 kg/h) fatty alcohol $C_{12-14}$ ($C_{12}$=65-71%, $C_{14}$=22-28%, C16=4-8%, molar weight=196

(from hydroxyl value) namely 201.11 kg/h=1.0261 kmol/h and 12.00 kg/h 50% caustic soda solution=6.00 kg/h 100% NaOH equivalent to 0.15 kmol/h=14.62 mol % related to fatty alcohol $C_{12-14}$. All together is fed after pre-mixing at a temperature of approx. 50° C. into a thin film evaporator (TFE) with a vaporizer surface of 1.0 m². The jacket temperature of the TFE is set by steam to 150° C.=approx. 4 bar (pressure controlled). The water from the caustic soda solution and the reaction water (in sum approx. 8.70 kg/h) to be distilled off is sucked out by a water jet pump under a vacuum of approx. 30 mbar. The formed sodium—fatty alcoholate $C_{12-14}$ with a rest water content of <0.05% is pumped out of the evacuated TFE and led over a slit filter to remove pollution. Then it is mixed in a static mixer with 2738.89 kg/h=13.9739 kmol/h fresh fatty alcohol $C_{12-14}$ (this mixture then contains 1.0 mol % sodium fatty alcoholate $C_{12-14}$.)

The supply temperature of the pressurized cooling/heating water loop with 10 m³/h is set in the upper jacket section at 112° C. The entrance temperature is adjusted under assistance of a "split range" control for supply of steam (especially for preheating) with constant pressure or cooling water into the pressure water loop. For the middle jacket a pressurized water loop of 10 m³/h and 150° C. is adjusted and also a 10 m³/h water loop with 150° C. for the lower section.

With a gear pump the fatty alcoholate $C_{12-14}$, catalyzed with 1.0 mol % is preheated over a heat exchanger to a temperature of 165° C. and charged over the two distributor slits (ring slit nozzles) with a quantity of 2943.30 kg/h (mass flow meter) fatty alcoholate $C_{12-14}$ (including formed alcoholate, which is the catalyst) evenly between the inner and outer reaction tube walls. Over a manifold on the reactor top 1980 kg/h=45.00 kmol/h ethylene oxide (relation fatty alcoholate $C_{12-14}$ to ethylene oxide=1 to 3) is charged by a pressure pump. Through the insert double tube (60% of the total length of the reactor=6.000 m) and over the previously mentioned annular gap cross sections inside and outside of the inserted double tube ethylene oxide is charged over the annular gaps (77.08%=1526.18 kg/h). The remaining quantity of ethylene oxide 453.82 kg/h=22.92% runs through the insert double tube approx. 6.000 m lower. The proportionate ethylene oxide conversion in the $1^{st}$ part of the reactor (35% of the reactor length) should be 57%, 28% in the $2^{nd}$ part (35% of the reactor length) and 15% in the $3^{rd}$ (30% of the reactor length). The reaction mixture then exits the post reactor (ring chamber approx. 0.08 m³) via a pressure control valve (adjusted to 50 bar) into a cyclone for degassing (inert gases from the EO, formed by-products e.g. dioxane). The waste gas exhausted by a water ring vacuum pump can be led to combustion or to a scrubber. Subsequently the cooling to approx. 60° C. takes place in a heat exchanger in the recycling loop to the cyclone.

For neutralization with 19.29 kg/h 70 weight % lactic acid (mole weight=90) the reaction mix is pumped over a dynamic mixer and passes a cooler in a loop (approx. 10 m³/h). The final product exiting the neutralizer loop flows into the storage tanks after filtering.

Example 7

Preparation of n-nonyl phenol ethoxylate with 3 mole ethylene oxide in a 36 inch annular gap reactor, with static mixing elements downstream the raw material input and at the second ethylene oxide input, 10 m long with insert double tube of 5.500 m length (55% of the total reactor length) and 1 mol % catalyst according to the invention with a capacity of 5707 kg/h, which corresponds to 45656 tons/year.

Compared with Example 6, the ethoxylation is performed in a 36 inch annular gap reactor with a length of 10 m and a catalyst concentration of 1 mol % and a length of the inserted double tube of 5.5 m (55% of the total length). In this case the reactor is used concurrently for pre heating of the ethylene oxide and fatty alcohol. The feeding temperature of the ethylene oxide is 20° C., and the temperature of the fatty alcohol with 1 mol % catalyst is 40° C.

The annular gap reactor according to FIGS. 1 and 2 consists of an outer tube with an inner diameter of 36 inches=914.4 mm and an inner tube with an outer diameter of 895.2 mm, and a reactor length of 10 m; with an annular width of 9.6 mm (annular space volume is 0.272 m³) and a raw material distributor slit (rings slit nozzle) in the inner and outer jacketed reaction tube and three cooling/heating sections (see FIG. 1). The upper and middle jackets each cover 35% and the lower jacket covers 30% of total reactor length. In the annular gap (annular space) a thin-walled double tube is incorporated. The inner and outer wall thickness of the reactor amounts to 19 mm, the gap of the cooling/heating jackets amounts to 8 mm and the volume of the post reactor amounts to 0.08 m³. The inner and outer wall thickness of the insert double tube is 0.5 mm, the outer diameter is 908.0 mm, the inner diameter is 901.6 mm, so that the gap width amounts to (908.0−901.60)/2=3.20 mm. The length of the insert double tube amounts to 5.500 m=55% of the total reactor length. The diameter of the insert double tube is dimensioned so that 77.08% of the ethylene oxide is charged over the inner and outer annular gap and the remaining 22.92% over the insert double tube cross section.

To manufacture the catalyst for Example 7, a part of the total raw material=3410.00 kg/h fatty alcohol $C_{12-14}$ ($C_{12}$=65-71%, $C_{14}$=22-28%, $C_{16}$=4-8%, molar weight=196 (from hydroxyl value) namely 233.26 kg/h=1.1901 kmol/h and 13.92 kg/h 50% caustic soda solution=6.96 kg/h 100% NaOH=0.1740 kmol/h=14.62 mol % related on fatty alcohol $C_{12-14}$. All is pre-mixed and fed at a temperature of approx. 50° C. into a thin film evaporator (TFE) with a surface of 1.0 m². The jacket temperature of the TFE is set by steam to 150° C.=approx. 4 bar (pressure controlled). The water from the caustic soda solution and the reaction water (in sum approx. 10.09 kg/h) to be distilled off is sucked out by a water jet pump under a vacuum of approx. 30 mbar. The formed sodium—fatty alcoholate $C_{12-14}$ with a rest water content of <0.05% is pumped out of the evacuated TFE and led over a slit to filter from pollution. Then it is mixed in a static mixer with 3176.74 kg/h=16.2078 kmol/h fresh fatty alcohol $C_{12-14}$ This mixture then contains 1.0 mol % sodium-fatty alcoholate $C_{12-14}$ as catalyst. The temperature of the mixture is 48° C.

The supply temperature of the pressurized cooling/heating water loop is set in the upper jacket section at 179° C. The loop quantity of water amounts to 10 m³/h. The entrance temperature is adjusted with assistance of a "split range" controlled steam pressure (especially for preheating) or cooling water supply into the pressure water loop. For the middle jacket a water loop of 10 m³/h and 113° C. is adjusted and for the lower jacket section a water loop with 167° C. is used.

By means of a gear pump the fatty alcoholate $C_{12-14}$, catalyzed with 1.0 mol % is charged over the two distributor slits (ring slit nozzles) in the inner and outer jacketed concentric reactor tubes with a quantity of 5710.83 kg/h (mass flow meter) with a mixing temperature of 48° C. equally between the inner and outer reaction tube walls. Over a head manifold on the reactor top 2297 kg/h ethylene oxide (=52.2045 kmol/h) (relation fatty alcoholate $C_{12-14}$ to ethylene oxide=1 to 3) is charged by a pressure pump. Through the insert double tube (55% of the total reactor length 5.500 m) and over the previously mentioned annular gap cross sections inside and outside of the inserted double tube ethylene oxide is charged (77.08%=1770.53 kg/h). The remaining quantity of ethylene oxide 526.47 kg/h=22.92% is charged through the insert double tube approx. 5.500 m below the top. The proportionate ethylene oxide conversion in the 1$^{st}$ part of the reactor (35% of the reactor length) should be 20%, 55% in the 2nd part (35% of the reactor length) and 25% in the 3rd (30% of the reactor length). The reaction mixture then exits the post reactor (ring chamber approx. 0.08 m$^3$) via a pressure control valve (adjusted pressure 50 bar) into a cyclone for degassing (inert gases from the ethylene oxide, formed by-products e.g. dioxane). The waste gas exhausted by a water ring vacuum pump can be led to combustion or to a scrubber. Subsequently cooling down to approx. 60° C. takes place by a heat exchanger in a recycling loop to the cyclone.

For neutralization with 22.37 kg/h 70% lactic acid (mole weight=90) the reaction mix is pumped over a dynamic mixer and passes a cooler in a loop (approx. 10 m$^3$/h). The final product exits the neutralizer loop and flows into the storage tanks after filtering.

What is claimed is:

1. A process for continuously reacting liquid alkylene oxide with a liquid substance comprising an organic compound with one or more active hydrogen atoms and a catalyst selected from alkali metal hydroxides and alkali metal alcoholates, in a reactor selected from
   (a) a tubular reactor comprising at least one reaction tube providing a reaction space inside of said tube, and
   (b) an annular-gap reactor comprising an outer tube and an inner tube, longitudinally inserted into said outer tube, which form an annular reaction gap extending between the inner surface of the outer tube, which forms the outer boundary of the reaction gap, and the outer surface of the inner tube, which forms the inner boundary of the reaction gap,
   wherein
   (1) the supply of liquid alkylene oxide to the reactor is controlled by a single mass flow controller, the liquid alkylene oxide is fed to said reactor (a) or (b) via a single inlet socket which is connected with a source of liquid alkylene oxide via said mass flow controller and the alkylene oxide is split before entering the reaction space or gap into a first and a second part,
   (2) said first part of alkylene oxide enters the reaction space or gap of said reactor (a) or (b) at a first location,
   (3) the liquid organic substance is injected to the interior of the reaction space of said tubular reactor (a) or to the interior of the reaction gap of said annular gap reactor (b) at a second location of the reactor, located at or downstream of said first location, and is intermingled with the liquid alkylene oxide to form a liquid reaction mixture, which moves downstream towards the end of the reactor,
   (4) the liquid alkylene oxide enters the reactor at said first location and over the entire-cross sectional area of the reaction space or gap at said location,
   (5) said second part of alkylene oxide is split off at said first location and is channeled from said first location to a third location in the reaction space or gap, through a separate tube in case of a tubular reactor (a) or through a separate double tube, respectively, in case of an annular gap reactor (b), which tube or double tube is inserted into the reaction space or gap, extends from said first location to said third location of the reactor space or gap, respectively, and has a diameter being smaller than the inner diameter of said reaction tube or outer boundary of said reaction gap, thus leaving a reaction space between the outer surface of said tube or double tube, respectively, on one side, and the inner surface of the reaction tube or the outer boundary of the reaction gap, respectively, on the other side,
   (6) said third location is located downstream of said second location and has a distance from said second location in flow direction of the reactor charge,
   (7) said second part of liquid alkylene oxide enters the reaction space or gap of the reactor at said third location and is intermingled with said liquid reaction mixture and reacts with it on its way downstream towards the end of the reactor and
   (8) the inner pressure of the reactor is kept at a pressure level where alkylene oxide entering the reactor does not vaporize,
   (9) ring slit nozzles are used to inject the liquid organic substance into the interior of the reaction space of said tubular reactor (a) or to the interior of the reaction gap of said annular gap reactor (b) and to mix it with alkylene oxide,
   (10) the intermixture of the liquid alkylene oxide with said liquid substance is further supported by one or more static mixing element(s) located at said second location and, optionally, by one or more further static mixing element(s) located between said second location and at said third location in the reaction space or reaction gap and/or the intermixture of the liquid alkylene oxide with said the liquid reaction mixture formed between said second and third location in the reactor is further supported by one or more static mixing element(s) located at said third and/or downstream of said third location in the reaction space or reaction gap,
   (11) the temperature of the reaction mixture is controlled by conveying liquid tempering media of suitable temperature through two or more separate tempering jackets, which are consecutively in longitudinal direction of the reactor fitted to the reaction tube(s) of said tubular reactor (a) or to the outer and inner tube of the annular-gap reactor (b), the first one of said tempering jackets being partially or completely located at a position between said second and third location, the second one being located directly after said first tempering jacket and partially or completely after said third location and the optional further tempering jackets following consecutively after said second tempering jacket,
   (12) the length of the insert tube or double tube ranges from 4 to 90 percent of the total length of the reaction space or gap,
   (13) the reactor has a length of 5 to 20 m,
   (14) wherein the double tube inserted into the reaction gap of said annular-gap reactor (b) has an annular cross section, which forms the entrance of said double tube for the alkylene oxide, which is channeled through said double tube and wherein the annular cross-sectional area of the inserted double tube at said first location is 90 to 10% of the sum of (A) the cross-sectional area of the inserted double tube at said first location, (B) the annular cross sectional area (I), extending from the outer surface of said inserted double tube to the outer boundary of the reaction gap, and (C) the annular cross section (II), extending from the inner boundary of the reaction gap to the inner surface of the inserted double tube.

2. The process according to claim 1, wherein the temperature of the reaction mixture in the reactor is maintained between 140-250° C.

3. The process according to claim 1, wherein the reaction mixture passes through an additional post reaction zone before leaving the reactor.

4. The process according to claim 2, wherein the reaction mixture passes through an additional post reaction zone before leaving the reactor.

5. The process according to claim 1, wherein the total quantity of liquid alkylene oxide reacted with said liquid substance is split so at said first location, that 50-95% of the alkylene oxide enter the reaction space or gap at said first location and the balance to 100% is channeled to said third location, enters the reaction space or gap at said third location and reacts with the reaction mixture formed upstream from said location.

6. The process according to claim 1, wherein the reactor is a tubular reactor (a).

7. The process according to claim 1, wherein the reactor is an annular gap reactor (b).

8. The process according to claim 7, wherein the double tube inserted into the reaction gap has a length of 4-70% of the length of the reaction gap.

9. The process according to claim 1, wherein the reactor is a tubular reactor (a) and the tube(s) inserted into the reaction tube(s) of said reactor has/have a length of 10-50% of the length of said reaction tube(s).

10. The process according to claim 1, wherein the inner pressure of the reactor is from 20 to 70 bar.

11. The process according to claim 1, wherein the liquid alkylene oxide is preheated to a temperature of 20 to 60° C. before it is fed into the reactor.

12. The process according to claim 4, wherein the total quantity of liquid alkylene oxide reacted with said liquid substance is split so at said first location, that 50-95% of the alkylene oxide enter the reaction space or gap at said first location and the balance to 100% is channeled to said third location, enters the reaction space or gap at said third location and reacts with the reaction mixture formed upstream from said location.

13. An apparatus for continuously reacting liquid alkylene oxide with a liquid substance comprising an organic compound with one or more active hydrogen atoms and a catalyst selected from alkali metal hydroxides and alkali metal alcoholates, comprising a reactor selected from
- (a) a tubular reactor comprising at least one reaction tube providing a reaction space inside of said tube, and
- (b) an annular-gap reactor comprising an outer tube and an inner tube, longitudinally inserted into said outer tube, which form an annular reaction gap extending between the inner surface of the outer tube, which forms the outer boundary of the reaction gap, and the outer surface of the inner tube, which forms the inner boundary of the reaction gap, and a source of liquid alkylene oxide which is connected with a line for said alkylene oxide via a single mass flow controller to a single inlet socket of said tubular reactor (a) or said annular gap reactor (b) for the alkylene oxide, wherein said reactor comprises (1) at the reactor head an inlet for the alkylene oxide to the reaction space of the at least one reaction tube of said tubular reactor (a) or the reaction gap of said annular gap reactor (b) which is connected to said inlet socket and extends over the entire cross-sectional area of the said reaction space or gap at a first location of said reaction space or gap, (2) a ring slit nozzle for injecting said liquid substance to the interior of the at least one reaction tube of the tubular reactor (a) and mixing it with alkylene oxide, which is located in said reaction tube at a second location at or downstream of said first location of the reaction space, or two ring slit nozzles for injecting said liquid substance to the interior of the reaction gap of said annular gap reactor (b) and mixing it with alkylene oxide, one ring slit nozzle being located in said outer tube and the other in said inner tube, which form the boundaries of the reaction gap, at a second location at or downstream of said first location of the reaction gap, (3) a tube inserted into each of the at least one reaction tube in case of a tubular reactor (a), or a double tube inserted into the reaction gap in case of an annular gap reactor (b), which extends from said first location in direction of the outlet of said reactor for the reaction product to a third location in the reaction space or gap having a distance from said first and second location, which tube or double tube channels liquid alkylene oxide from said first location to said third location to dispense it at said location to the reaction space or gap, wherein said tube or double tube has a diameter being smaller than the inner diameter of said reaction tube or outer boundary of said reaction gap, thus leaving reaction space between the outer surface of the tube or double tube, respectively, on one side, and the inner surface of the reaction tube or the outer boundary of the reaction gap, respectively, on the other side, (4) one or more static mixing element(s) located at said second location and, optionally, one or more further static mixing element(s) located between said second location and said third location in the reaction space or reaction gap for supporting the intermixture of the liquid alkylene oxide with said liquid substance and/or one or more static mixing element(s) located at said third and/or downstream of said third location in the reaction space or reaction gap for supporting the intermixture of the liquid alkylene oxide with the liquid reaction mixture formed between said second and third location in the reactor, (5) two or more separate tempering jackets, which are consecutively in longitudinal direction of the reactor fitted to the reaction tube(s) of said tubular reactor (a) or to the outer and inner tube of the annular-gap reactor (b), the first one of said tempering jackets being partially or completely located at a position between said second and third location, the second one being located directly after said first tempering jacket and partially or completely after said third location and the further tempering jackets following consecutively after said second tempering jacket, and (6) an outlet for the reaction product at a location in the reaction space or gap which is downstream from all said other locations, (7) the length of the insert tubes or double tubes ranges from 4 to 90 percent of the total length of the reaction space or gap (8) the reactor has a length of 5 to 20 m, wherein (9) the double tube inserted into the reaction gap of said annular-gap reactor (b) has an annular cross section, which forms the entrance of said double tube for the alkylene oxide, which is channeled through said double tube, and wherein the annular cross-sectional area at said first location is 90 to 10% of the sum of (A) the cross-sectional area of the inserted double tube at said first location, (B) the annular cross sectional area (I), extending from the outer surface of said inserted double tube to the outer boundary of the reaction gap, and (C) the annular cross section (II), extending from the inner boundary of the reaction gap to the inner surface of the inserted double tube.

14. The apparatus according to claim 13, comprising three separate tempering jackets.

15. The apparatus according to claim 14, wherein said tubular reactor (a) or said annular-gap reactor (b) comprise an additional post-reaction space located between the reaction tubes and the outlet for the reaction product in case of a tubular reactor or, in case of an annular gap reactor (b), in a zone of the reactor following the main reaction gap between the inlet for the liquid catalyzed raw material and the end of the—in direction to the outlet of the reactor—last of said tempering jackets mounted to the reactor.

16. The apparatus according to claim 15, comprising an annular gap reactor (b) which comprises an additional post-reaction space wherein the inside width of the annular gap is larger than the inside width of the main reaction gap.

17. The apparatus according to claim 13, wherein the cross-sectional area of the single tube or double tube is from 50 to 5% of the sum of said cross-sectional area and the cross-sectional area of the reaction space or gap at the first location.

18. The apparatus according to claim 13, wherein the double tube inserted into the reaction gap has a length of 4-70% of the length of the reaction gap.

19. The apparatus according to claim 13, wherein the reactor is a tubular reactor (a).

20. The apparatus according to claim 19, wherein the tube(s) inserted into the reaction tube(s) of said reactor has/have a length of 10-50% of the length of said reaction tube(s).

21. The apparatus according to claim 13, comprising a reactor having a total length of 5 to 15 meter.

22. The apparatus according to claim 13, wherein said single inlet socket for the alkylene oxide of the tubular reactor (a) or the annular gap reactor (b) is connected to a source of liquid ethylene oxide, a source of liquid propylene oxide or a source of a mixture of liquid ethylene and propylene oxide.

\* \* \* \* \*